(12) United States Patent
Baumberg et al.

(10) Patent No.: US 7,483,130 B2
(45) Date of Patent: Jan. 27, 2009

(54) METAL NANO-VOID PHOTONIC CRYSTAL FOR ENHANCED RAMAN SPECTROSCOPY

(75) Inventors: Jeremy Baumberg, Winchester (GB); Sven Mahnkopf, Reno, NV (US); Majd Zoorob, Southampton (GB); John Lincoln, Wiltshire (GB); James Wilkinson, Southampton (GB)

(73) Assignee: D3 Technologies, Ltd., Edinburgh (GB)

( * ) Notice: Subject to any disclaimer, the term of this patent is extended or adjusted under 35 U.S.C. 154(b) by 164 days.

(21) Appl. No.: 11/267,619

(22) Filed: Nov. 4, 2005

(65) Prior Publication Data

US 2006/0119853 A1    Jun. 8, 2006

(30) Foreign Application Priority Data

Nov. 4, 2004   (GB) ................... 0424458.8
Jan. 21, 2005  (GB) ................... 0501342.0
May 3, 2005    (GB) ................... 0508964.4

(51) Int. Cl.
    *G01J 3/44*    (2006.01)
(52) U.S. Cl. ....................................... 356/301
(58) Field of Classification Search ................ 356/301; 428/469, 650, 364, 209, 558; 216/24
    See application file for complete search history.

(56) References Cited

U.S. PATENT DOCUMENTS

| 6,406,777 | B1 | 6/2002 | Boss et al. |
| 2003/0132392 | A1 | 7/2003 | Kuroda et al. |
| 2003/0173501 | A1 | 9/2003 | Thio et al. |

2004/0023046 A1   2/2004   Schlottig et al.

FOREIGN PATENT DOCUMENTS

| EP | 1580305 A2 | 9/2005 |
| WO | WO 98/25313 A1 | 6/1998 |
| WO | WO 02/08810 A2 * | 1/2002 |

(Continued)

OTHER PUBLICATIONS

Combined search and examination report for corresponding application GB 0522633.7, dated Jan. 31, 2006, 5 pages.

(Continued)

*Primary Examiner*—Kara E Geisel
*Assistant Examiner*—Abdullahi Nur
(74) *Attorney, Agent, or Firm*—Oliff & Berridge, PLC

(57) ABSTRACT

A planar optical platform for generating a Raman signal from a foreign object comprises an input region and an output region, for receiving and extracting optical radiation, optically coupled to a plasmonic band structure region. The plasmonic band structure region comprises a layer of a first material, having a first refractive index, patterned with an array of sub-regions of a second material, having a second refractive index, wherein a side-wall of each sub-region is coated with a metallodielectric layer. The array of sub-regions gives rise to a plasmonic band structure and, in use, each sub-region confines a plasmon resonance excited by optical radiation coupled into the plasmonic band structure region, which gives rise to a Raman signal from a foreign object placed proximate the plasmonic band structure region. The platform may be incorporated into a spectroscopic measurement system and is particularly useful for surface-enhanced Raman spectroscopy of analyte molecules.

39 Claims, 30 Drawing Sheets

FOREIGN PATENT DOCUMENTS

| WO | WO 02/42836 A1 | 5/2002 |
| WO | WO 03/106943 A1 | 12/2003 |
| WO | WO 2004/074790 A1 | 9/2004 |

OTHER PUBLICATIONS

International Search Report and Written Opinion of the ISA/EP for corresponding application PCT/GB2005/004260, dated Nov. 4, 2005, 14 pages.

Moran, C., et al., "Chemical and Dielectric Manipulation of the Plasmonic Band Gap of Metallodielectric Arrays," Nano Letters, American Chemical Society, Aug. 2004, 4(8):1497-1500.

Coyle, S., et al., "Localised Plasmons in Gold Photonic Nanocavities," Technical Digest, Summaries of Papers Presented at the Quantum Electronics and Laser Science Conference, Opt. Soc. America, 2002, vol. 1, p. 257, Washington, D.C., US.

Liu, Y., et al., "Biosensing based upon molecular confinement in metallic nanocavities," Nanophotonics and Biomedical Applications, Proceedings of SPIE—The International Society for Optical Engineering, 2004, vol. 5331, pp. 68-75, Alexander N. Cartwright, ed.

Coyle, S., et al., "Confined Plasmons in Metallic Nanocavities," Physical Review Letters, American Physical Society, Oct. 22, 2001, 87(17):176801-1 through 176801-4, New York, US.

Puscasu, I., et al., "Frequency Selective Surfaces Enable MEMS Gas Sensor," Materials Research Society Symposium Proceedings, Materials Research Society, Apr. 1, 2002, vol. 722, pp. 395-400, Pittsburgh, PA, US.

Search report for priority application GB 0424458.8, dated Feb. 11, 2005.

Search report for priority application GB 0501342.0, dated May 20, 2005.

* cited by examiner

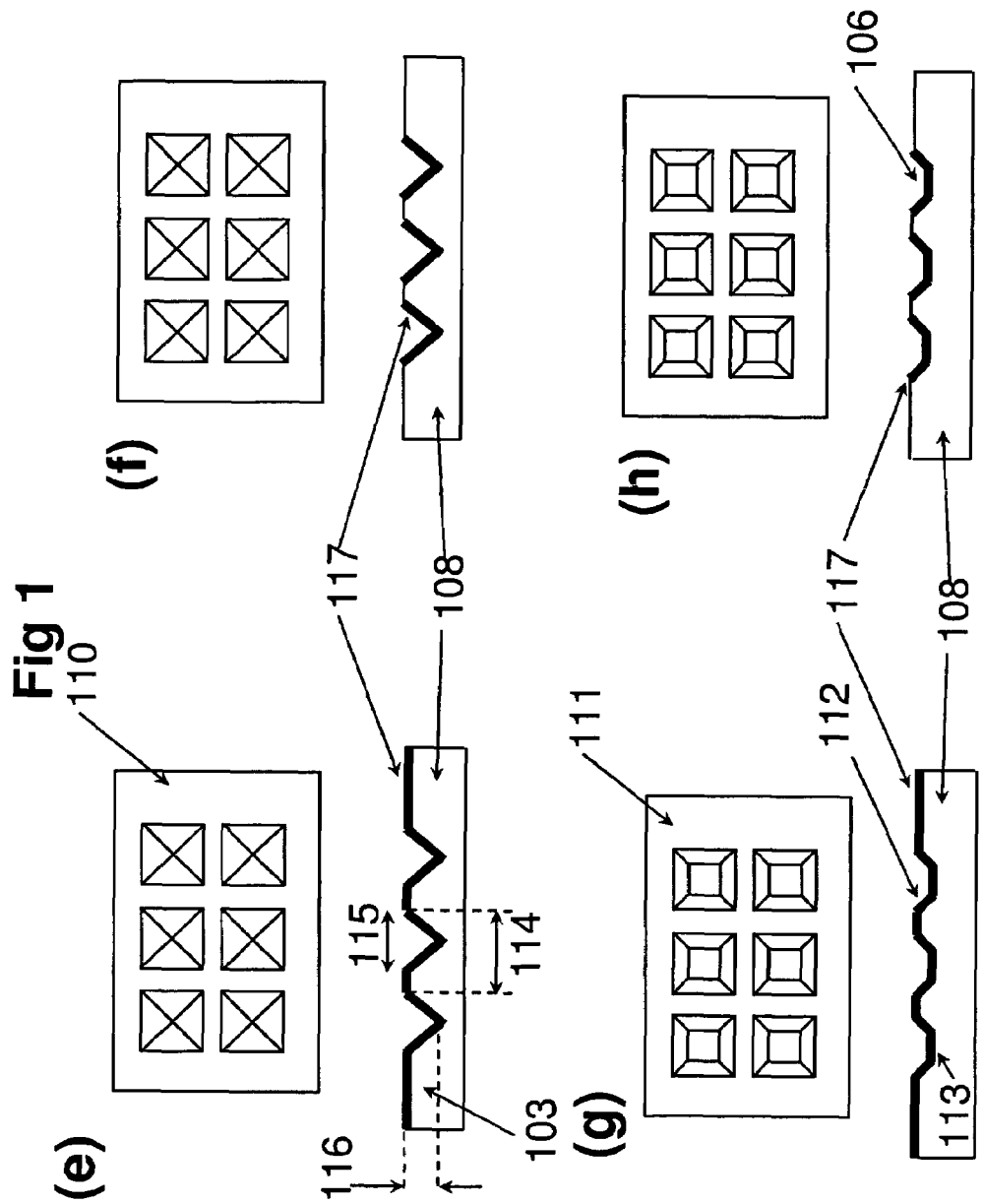

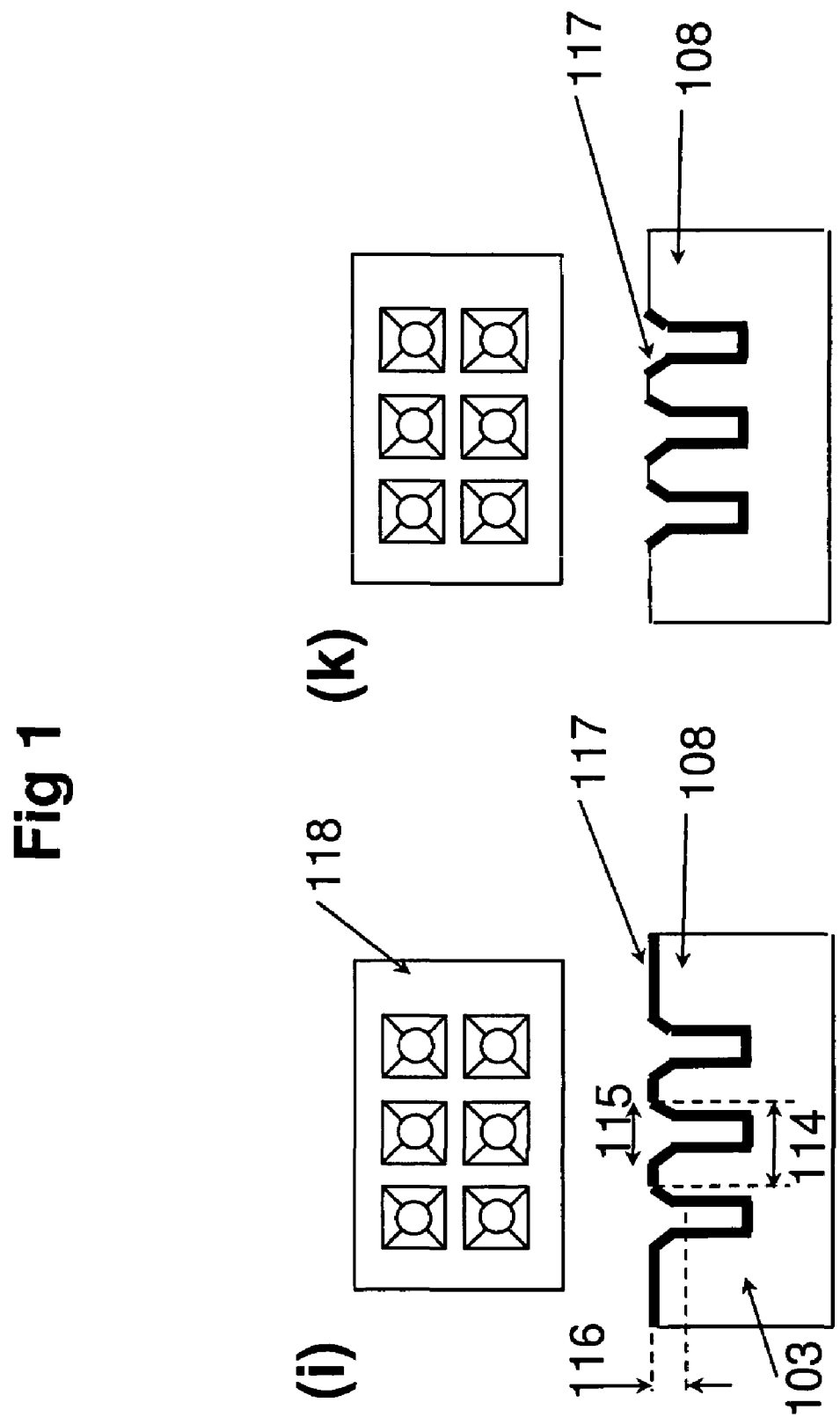

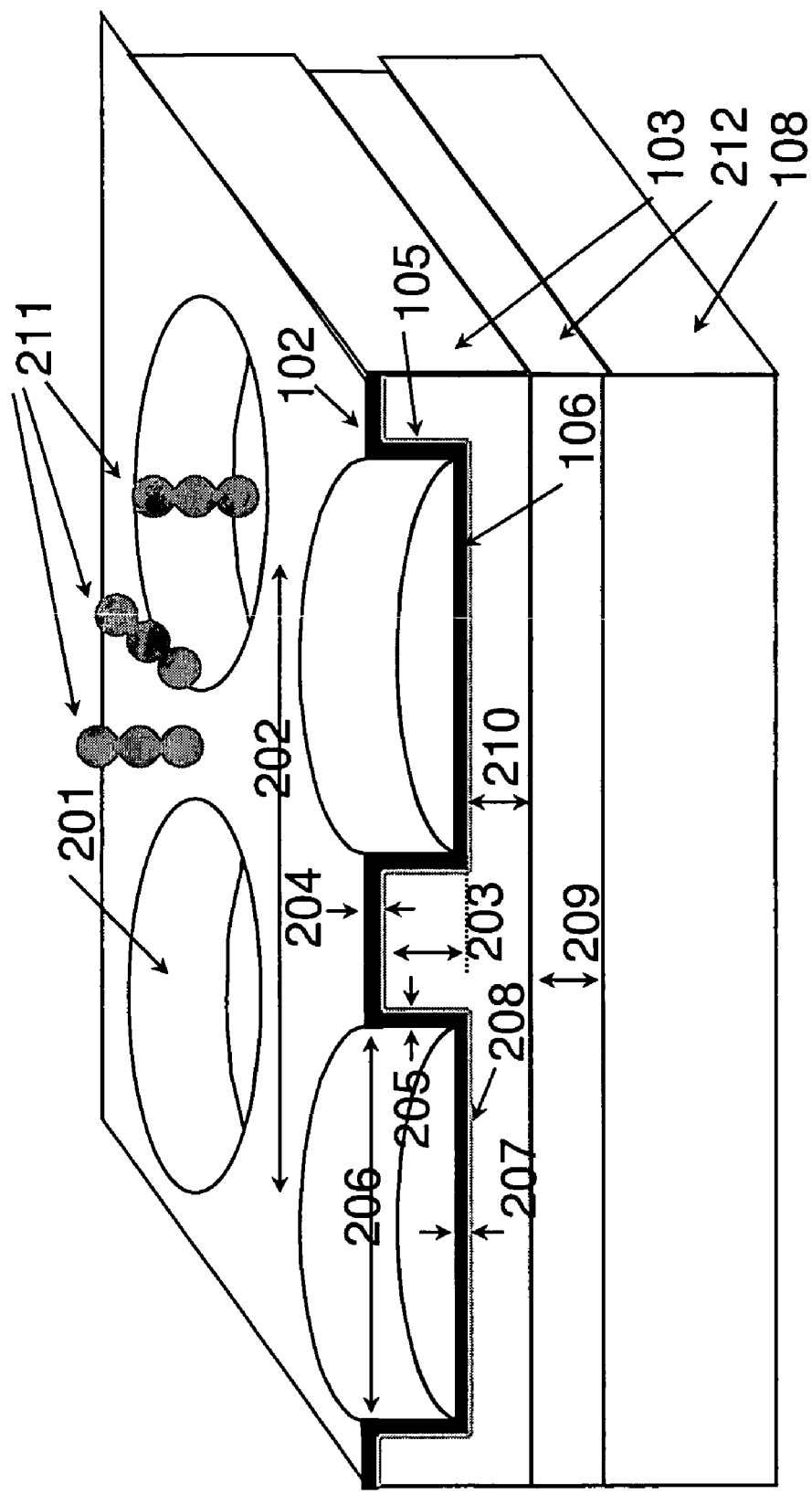

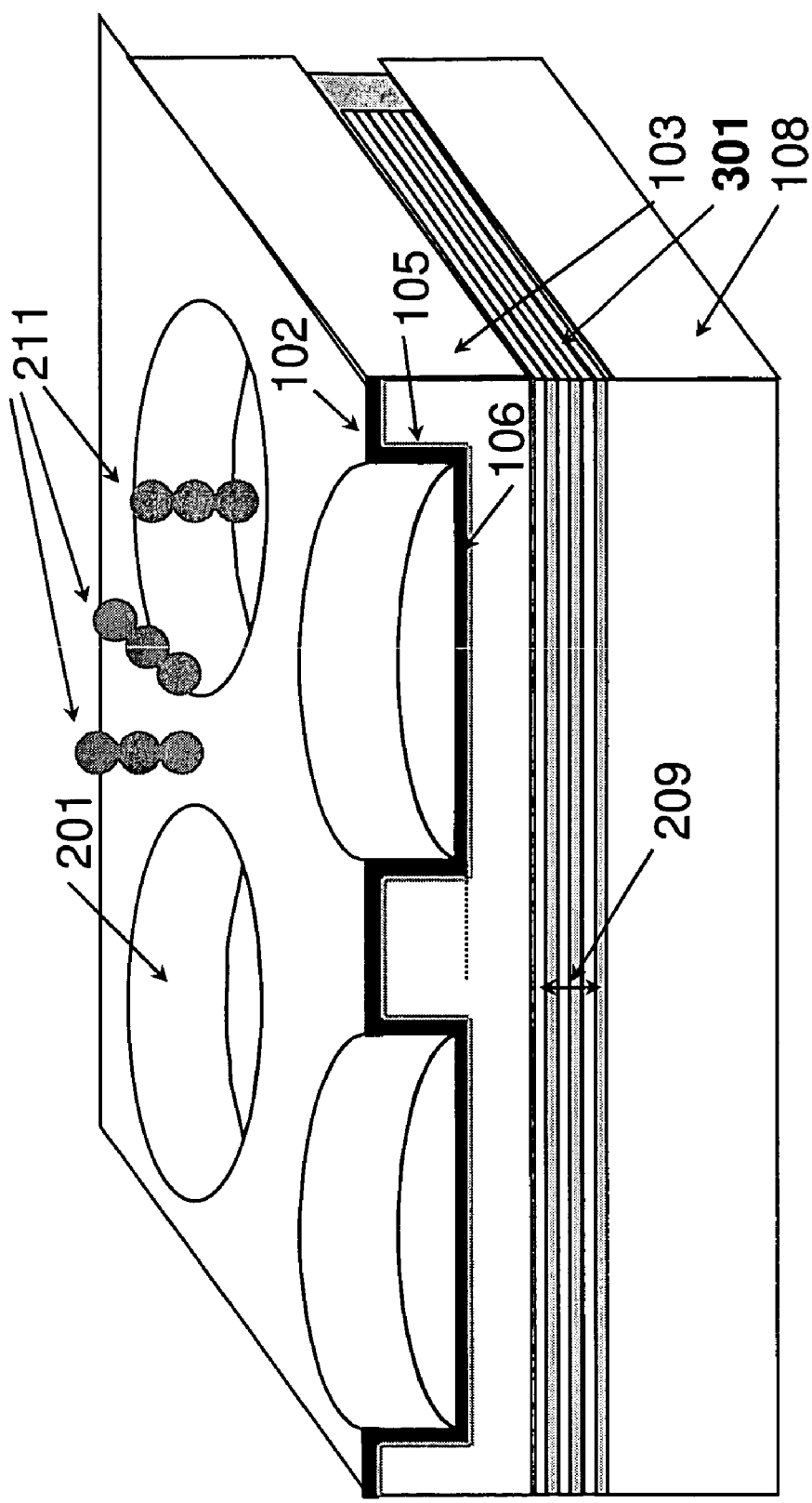

Fig 4
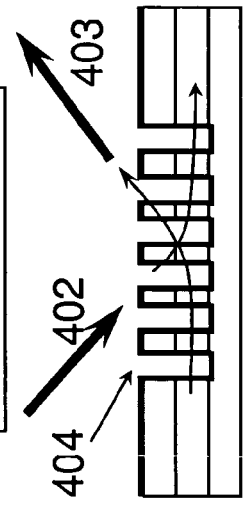
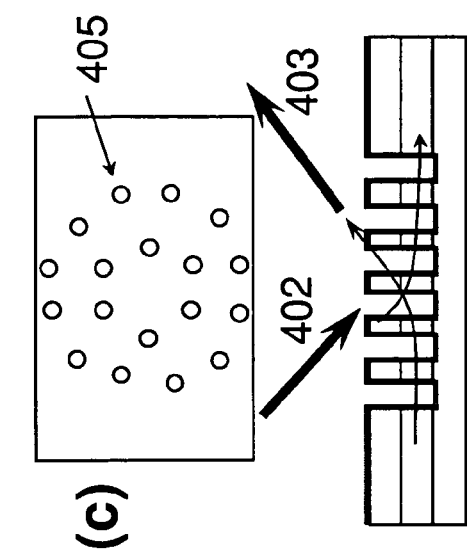
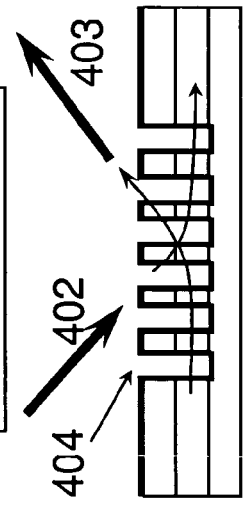
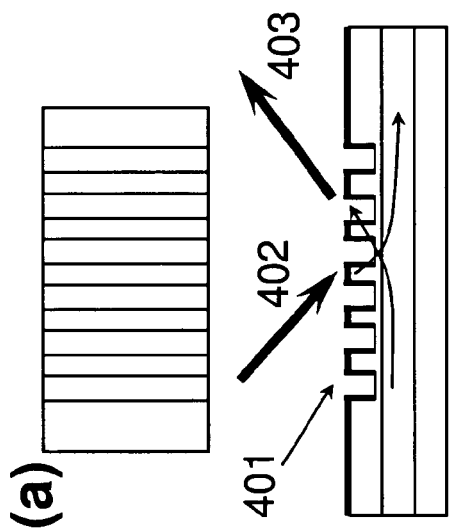

Fig 8B
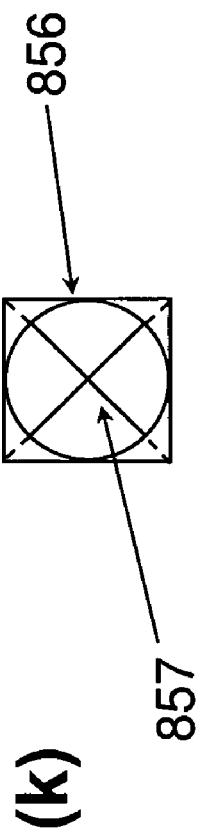
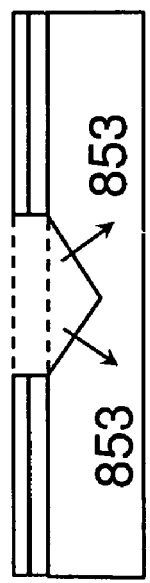
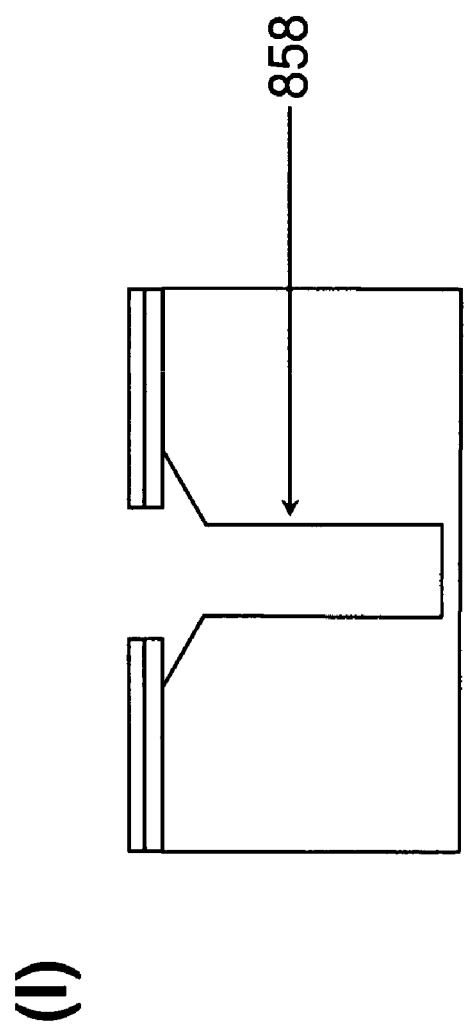
(k)
(l)

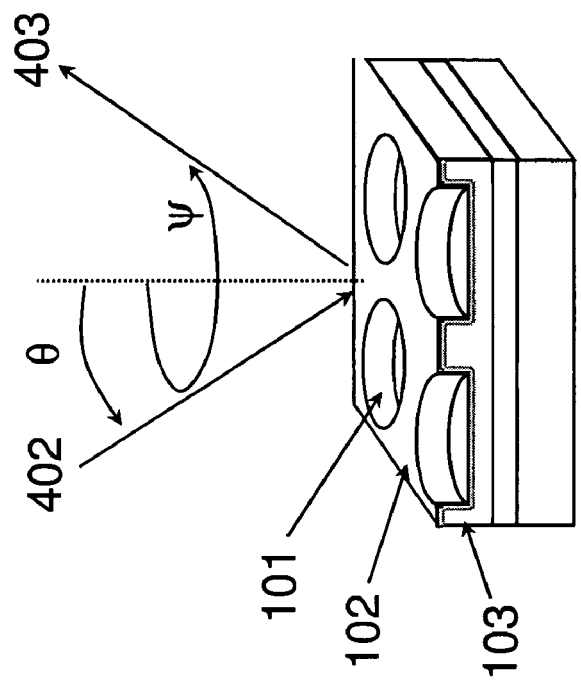
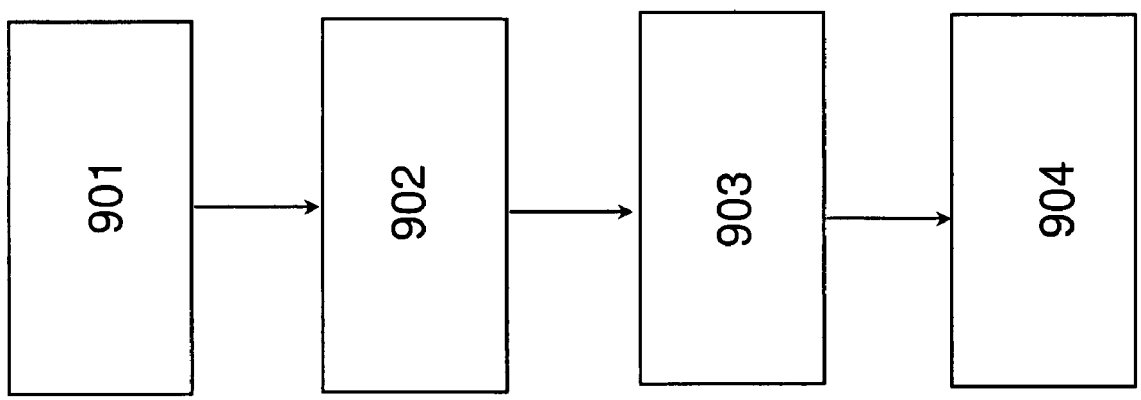
Fig 9

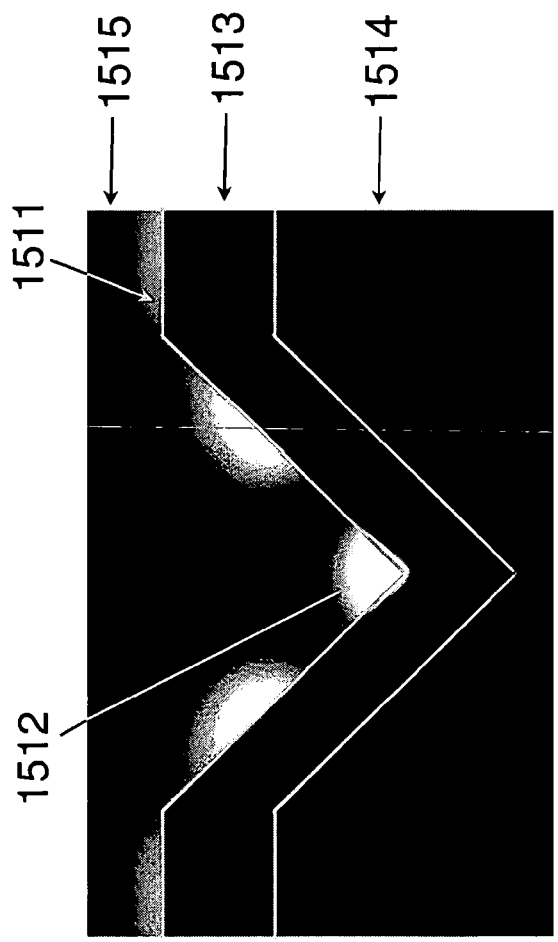
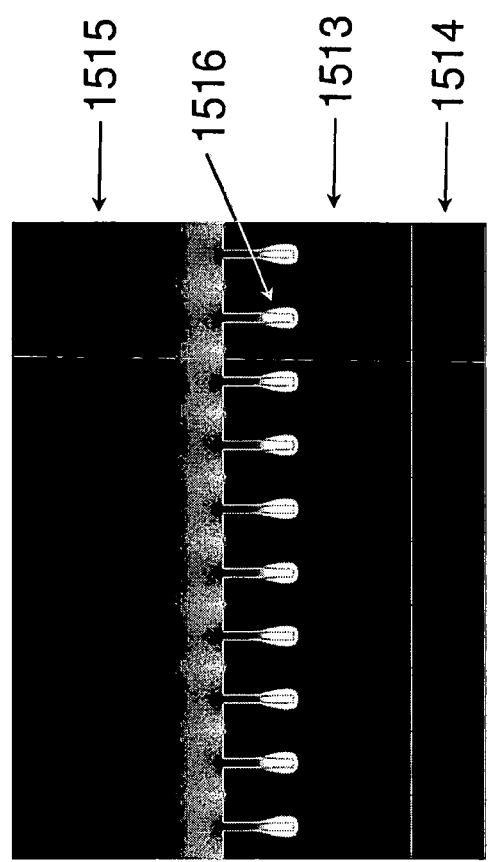
Fig 15A
Fig 15B

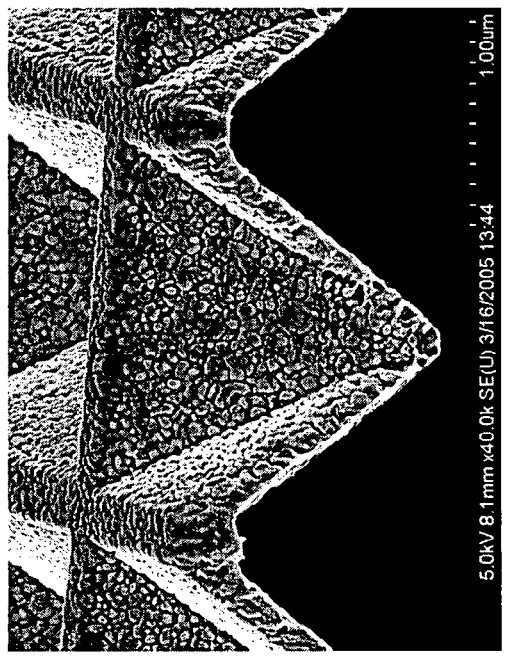
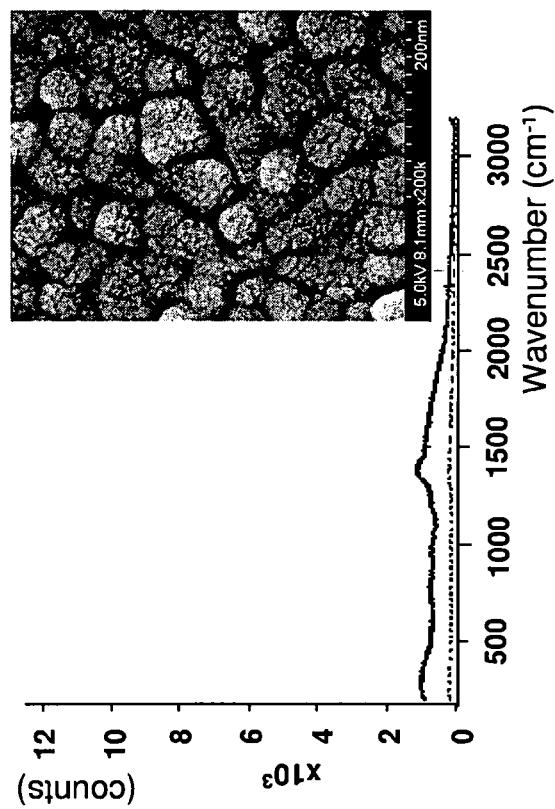
Fig 17A
Fig 17B

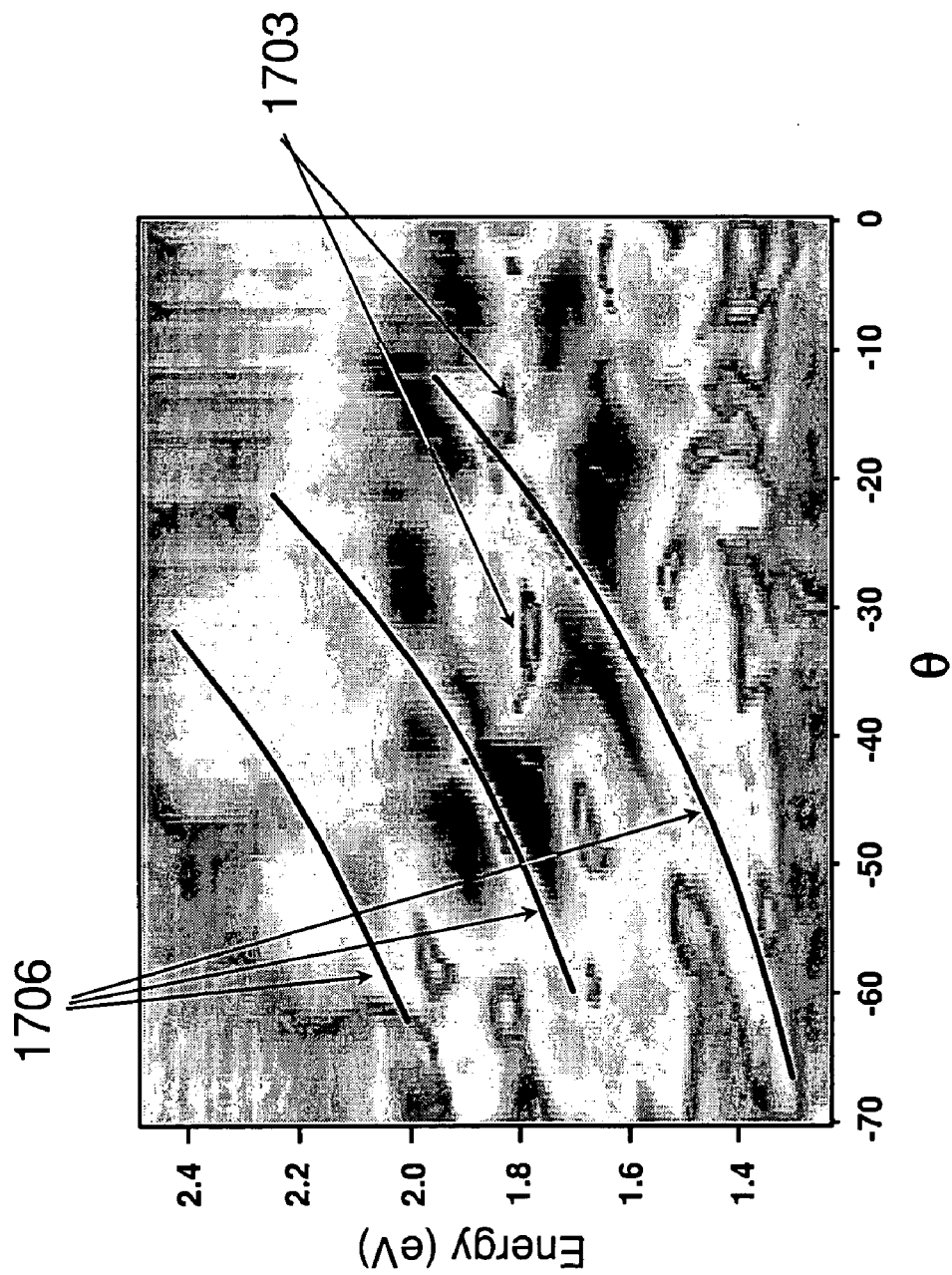

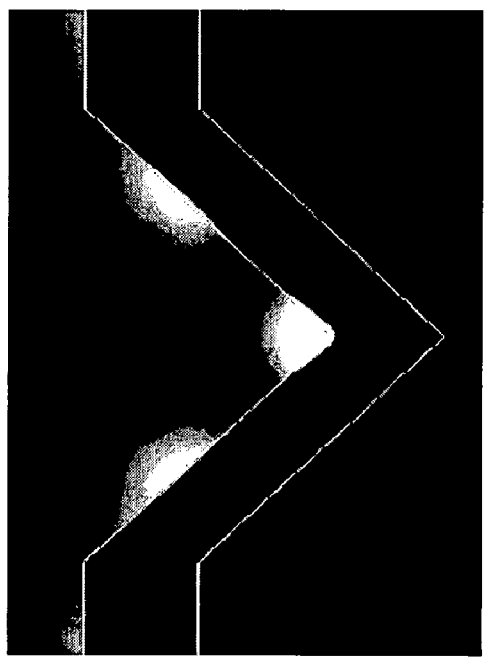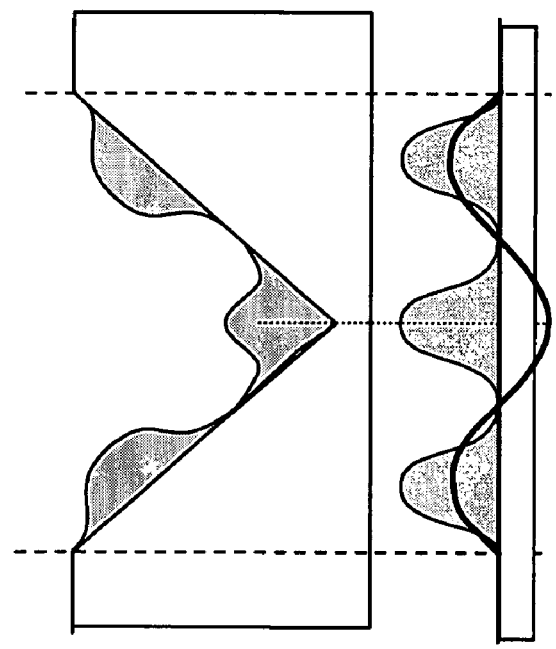
Fig 18D
Fig 18E

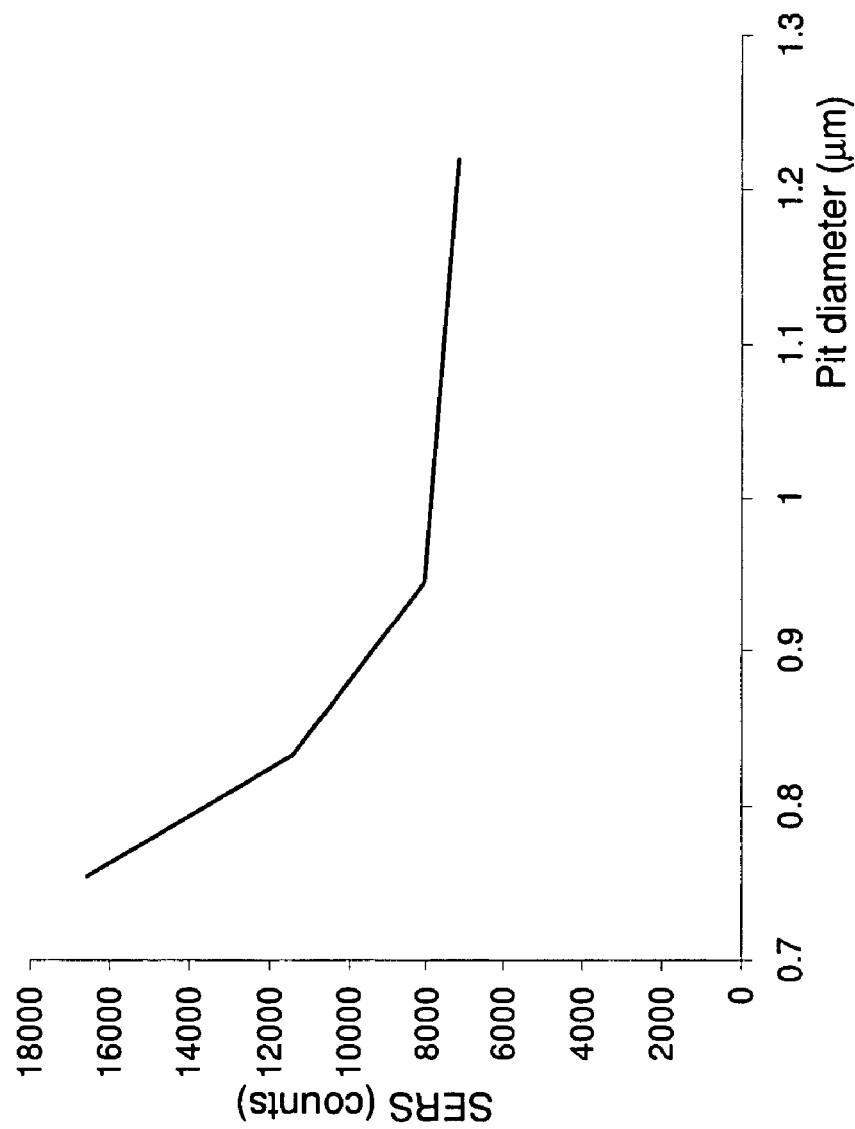

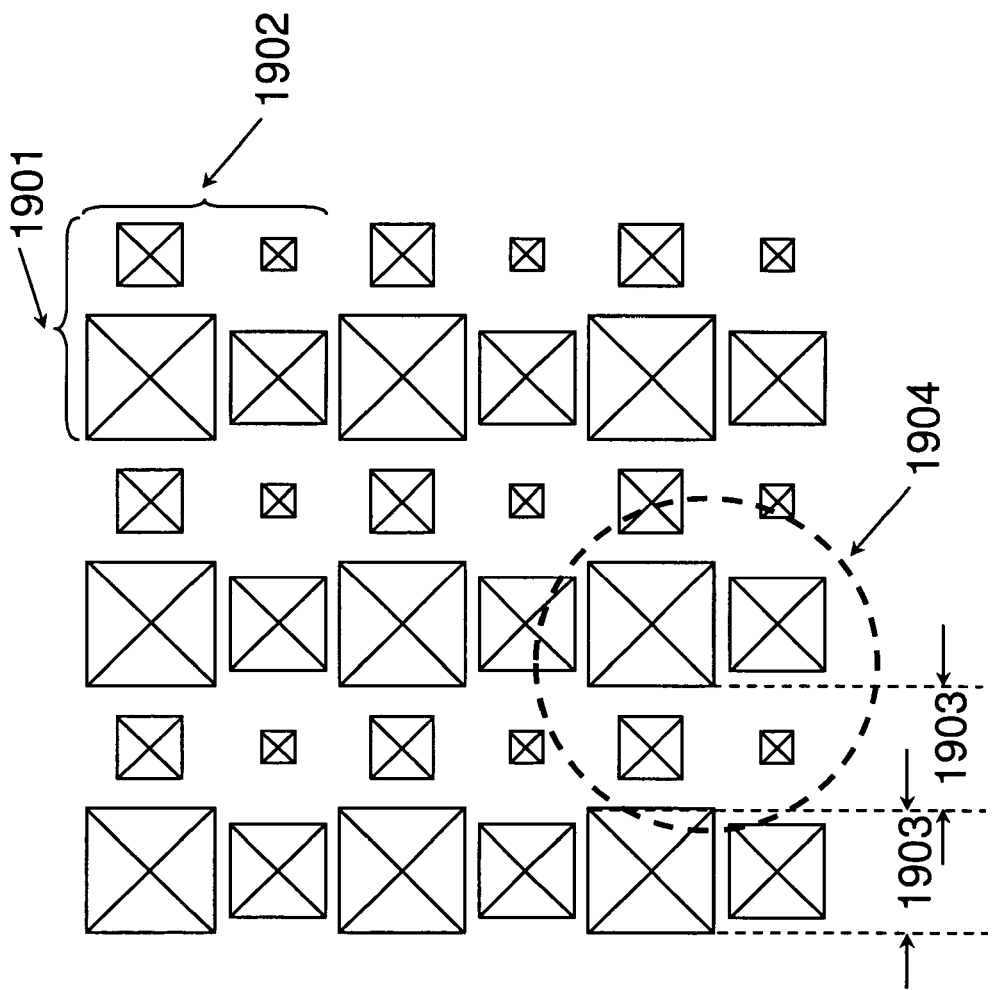

METAL NANO-VOID PHOTONIC CRYSTAL FOR ENHANCED RAMAN SPECTROSCOPY

FIELD OF THE INVENTION

The invention relates to Raman spectroscopy, and, in particular, to an optical platform for surface enhanced Raman spectroscopy (SERS).

BACKGROUND

Raman spectroscopy is used for a variety of applications, most commonly to study vibrational quanta, such as vibrations in molecules or phonons in solids, although other quantised entities can also be studied. Raman spectroscopy can provide detailed information relating to the physical state of sample materials and can be used to distinguish various states of otherwise chemically identical molecules, such as various molecular isomers, from one another.

Raman spectroscopy finds wide-ranging use in numerous different industries. By way of example, Raman spectroscopy finds application in the pharmaceutical, chemical, bio-analysis, medical, materials science, art restoration, polymer, semiconductor, gemmology, forensic, research, military, sensing and environmental monitoring fields.

Although Raman spectroscopy is an extremely useful analytical tool, it does suffer from a number of disadvantages. The principal drawbacks associated with Raman spectroscopy arise because of the small scattering cross-section. Typically, only $10^{-7}$ of the photons incident on the sample material will undergo Raman scattering. Hence, in order to detect Raman scattered photons, Raman spectrometers typically employ high power laser sources and high sensitivity detectors. Not only is the scattering cross-section small in an absolute sense, but it is small relative to Rayleigh scattering in which the scattered photon is of the same energy as the incident photon. This means that there are often problems related to separating out the small Raman signal from the large Rayleigh signal and the incident signal, especially when the Raman signal is close in energy to the incident signal.

High power sources are not only both bulky and expensive, but at very high power the intensity of the optical radiation itself can destroy the sample material, thus placing an upper limit on the optical radiation source intensity. Similarly, high sensitivity detectors are often bulky and expensive, and even more so where forced cooling, such as with liquid nitrogen, is necessary. Additionally, detection is often a slow process as long integration periods are required to obtain a Raman spectrum signal having an acceptable signal-to-noise ratio (SNR).

The problems associated with Raman spectrometry have been known long since C. V. Raman discovered the effect itself in 1928. Since that date, various techniques have been applied to improve the operation of Raman spectrometers.

Certain of the techniques involve the use of metal surfaces to induce surface plasmon resonance (SPR) for more efficient coupling of energy into the sample material. One refinement of this technique involves placing sample material on or near a roughened surface. Such a surface can be formed by the deposition of metallic/dielectric particles, sometimes deposited in clusters. The roughened surface is found to give rise to an enhanced Raman signal, and the technique of using the roughened surface to obtain a Raman spectrum is known as surface enhanced Raman spectroscopy (SERS).

However, while SERS devices can lead to an improved SNR when compared to previous conventional Raman spectrometers, they still suffer from other drawbacks. For example, SERS devices are still not efficient enough to provide a Raman signal without fairly long detector integration times, and still require the use of bulky and expensive detectors. Even at present, an acquisition time for a Raman spectrum of some five seconds is considered to be extremely good. A major problem of many of the presently used SERS systems is the reproducibility of SERS enhancements with repetitions of the same experiment and between different samples. This is largely due to the random distribution and number of hot spots available on the roughened surface and the inability to predetermine their location.

US 2003/042487 describes a method of providing metal objects selected from nanowires, nanorods, and spheroids. This is proposed to surface enhance the spectroscopy of biomolecules in close proximity to the metal objects.

US 2003/059820 discloses the method, system, and method of fabrication of a substrate comprising of metal-coated nanoparticles including nanospheres, nanoparticles, nanorods (see the example shown in FIG. 7(b)).

US 2003/174384 and U.S. Pat. No. 6,699,724 discuss the use of metal-coated spheres and nanoparticles as substrates to enhance the Raman signal from an analyte in close proximity to the substrate.

US 2002/068018 discloses a sensor for the detection of chemical and/or biological compounds consisting of a plurality of high-Q electromagnetic microcavities. It is claimed that a similar effect to SERS results in the detection of the biological agent.

US 2004/180379 discloses a nanobiosensor based on SERS, while U.S. Pat. No. 6,579,721 discusses a method of biosensing using surface plasmon resonances from perforated metal film located on a glass substrate (as illustrated in FIG. 7(a)). U.S. Pat. No. 6,759,235 discloses a device consisting of closely packed array of collimated holes distributed across a surface used for immobilizing beads to generate spectra in response to some external excitation energy.

Finally, M. Kahl et al. (Phys. Rev. B, vol. 61, no. 20, art. 14078) discuss the use of metal coated 1 D gratings to enhance the Raman signal off a surface and P. Etchgoin et al. (J. Chem. Phys., vol. 119, no. 10, p. 5281) elaborate on the electromagnetic contribution to SERS in view of photonic crystal concepts through an analysis of the energy distribution and spatial localization of surface plasmon resonances to provide a qualitative understanding of some known SERS phenomena. The success of nonresonant excitation in the electromagnetic contribution to SERS is explained and physical phenomena utilizing the stimulation or inhibition of the Stokes/anti-Stokes fields are proposed. W. L. Barnes et al. (Nature, vol. 424, p. 824) provide an overview on the impact of surface plasmons with regard to various applications.

As such, the role of surface plasmon polaritons (SPPs) in the understanding of extraordinary transmission properties of light through a metal film perforated with subwavelength apertures has been recognized, and the application of this effect in the context of SERS has been identified. However, the combination of SPPs propagating inside holes, SPPs propagating on metal interfaces and localized SPs bound to surface defects (and couplings thereof) have not been explored in the context of enhancing the Raman signal for use as a biosensor. Additionally, the potential benefits of separating the light collection and extraction from the Raman signal generation, and the possible monolithic integration of signal preparation functions before and after the Raman generating process, have not been clearly identified by researchers in the field.

SUMMARY

The present system provides a platform, system, and method for surface enhanced Raman spectroscopy that provides reproducible Raman signal enhancements for a low concentration of analyte molecules as well as the added functionality of pre- and post-processing which can be integrated on a single platform. Also provided is a method of mass fabrication of the platform In a new implementation put forward herewith, metallodielectric photonic crystals (PC) are used to extract a SERS signal from low concentrations of analyte molecules embedded inside the PC lattice.

The present system encompasses four main aspects, namely a photonic crystal (PC)-based SERS active platform, a system and method for obtaining a SERS signal from an analyte, and a fabrication method for the PC-based SERS platform.

The SERS active platform is based on a coated modulated substrate, whereby an array of holes, polyhedra or wells is embedded in a dielectric multilayer system. The dielectric multilayer system can be isotropic in its simplest implementation but can also form a distributed Bragg reflector (DBR) or planar waveguide structure. The holes or polyhedra can be located either above the dielectric multilayers, but can also partially or fully penetrate the same. The holes can be arranged in a regular 2D photonic crystal lattice topology such as a triangular, square, or rectangular lattice geometry, a graded or doubly graded 2D PC lattice, a quasi-periodic 2D PC lattice, or a 2D PC lattice with one or more defects. The polyhedra are typically inverted pyramids (in some cases, be truncated, inverted polyhedra) that reside on the surface of the dielectric multilayer system and penetrate into the layers. The coating is generally metallic but can also contain other metallic or dielectric layers.

In a preferred embodiment, the metallodielectric layer consists of an optically thin layer of a noble metal. In another embodiment, the platform is arranged in a membrane configuration in which the SERS active region is located above an air cavity. In both the membrane and solid substrate embodiments, the metallodielectric layer can be continuous across both the top surface and the sidewalls of the holes or can only cover the sidewalls of the holes or polyhedra while the top surface is deficient of any metallic coating. The platform may furthermore contain one or more functional system blocks such as pre- or postprocessing and/or the sensor and light source unit. The pre- and postprocessing units may be infiltrated with an electrically tunable material, thus facilitating the possibility for an electrical control of the pre-/postprocessor function. Adjacent on-chip system blocks may be combined into an integrated structure.

The system consists of the following seven functional blocks: a light source, a pre- and postprocessing device, structures for receiving and extracting optical radiation, said SERS active platform, and an optical detector system. The functions of the preprocessor can include the selection of the incident beam parameters such as incident polar and azimuthal angles, denoted as $\theta$ and $\psi$, respectively, as illustrated in FIG. 9, the polarization state and incident wavelength $\lambda_i$. The post-processing unit can for example filter out the pump light to improve the SNR, introduce a wavelength-dependent optical time delay or contain a superprism for spatial resolution of the Raman response, just to name a few possibilities. As mentioned with respect to the platform, some of the system's functional blocks may be monolithically integrated into a densely integrated optical sensor chip.

The method describes the means of obtaining the SERS signal for the analysis and detection of an analyte. Analytes can include chemical warfare agents, pesticides, urea, lactic acid, pollutants, ascorbate, and glucose, or biomolecules such as proteins, lipids, nucleic acids (bacterial and viral DNA, RNA, PNA and others) or cellular matter. After filling of the SERS substrate with the analyte under investigation and activation of the light source, the SERS signal is detected using a spectrometer. The spectrometer can be a commercially available spectrometer but may also be monolithically integrated onto the biochip. Light may be incident either out-of-plane or can be launched into a planar waveguide from where it is coupled to the SERS active region. Similarly, light can be collected either out-of-plane or coupled into an underlying waveguide plane and guided to a spectrometer.

In a final aspect, there is provided a method for the mass fabrication of said SERS active platform. Preferably, mass fabrication employs wafer-scale Silicon-compatible fabrication techniques. The PC can be fabricated by imprint in a resist coat on top of a dielectric substrate such as Silicon and subsequent etching of cylindrically shaped pores into the substrate using a highly anisotropic etch process. The imprint step allows a cheap fabrication, which can be easily scaled to large volume production. Alternative means to define the PC lattice structure are lithographic techniques such as photolithography, interference lithography, or electron beam lithography. Subsequent deposition of one or more metallo-dielectric layers either exclusively inside the pores or both inside the holes and on top of the sample surface creates the SERS active region.

In a preferred method of fabrication, the lattice pattern definition is applied on the surface of a dielectric substrate comprising of a crystalline Silicon wafer oriented along a specific crystal plane. The wafer is subsequently anisotropically etched typically using a wet etching process. The anisotropic wet etching forms polyhedral shapes where the exposed polygon surfaces of the polyhedra lie along the {111} crystal plane face of the Silicon. Subsequently the application of the metallo-dielectric layers is performed.

In a preferred orientation of Silicon single crystal wafer, a wafer exposed along the {100} crystal plane is selected. During the subsequent anisotropic wet etching inverted pyramids are formed. The etch process will stop once all polyhedra faces are along the {111} crystal planes of the substrate.

In another embodiment, the method of fabrication is extended to also include an isotropic deep Silicon etch following the anisotropic wet etch. This provides high aspect ratio holes located at the centre of the polyhedra.

In a further embodiment, the plasmonic bandstructure region may be designed to provide a means of maintaining a high reproducibility SERS signal even when roughness corrugations are experienced on the surface of the metallodielectric Photonic Crystal. The roughness corrugations arise from the fabrication deposition methods and vary randomly. It is known in the prior art that surface roughness is one contributory source of generation of a SERS signal. However, the randomness of the roughness generates regional hot spots where SERS is formed, and hence can cause large fluctuation in the SERS signal at different locations on the SERS substrate (>100% standard deviation of SERS signal). In the present embodiment, high reproducibility is achieved by optimizing the plasmonic bandstructure properties to maintain surface and localized plasmons substantially associated with the large scale patterned features of the plasmonic bandstructure rather than the small scale features of the nanoscale surface roughness (<100 nm).

In yet another embodiment, the plasmonic bandstructure region is designed to possess repeating arrays of sub-regions, each sub-region possessing multiple inverted polyhedra or holes of different sizes and shapes. Each size and shape will provide a different localised plasmon resonance and hence allows increased coupling efficiency to input laser light of any wavelength and enhanced output coupling of Raman light of different wavelengths. This in turn provides improved reproducibility of the output SERS signal.

Major improvements provided by the present system compared to many prior art systems include the following aspects. The topologies allow the launch of light from the side, hence facilitating easier and more reproducible means of launching light to the SERS active region. Secondly, the integration of many functional system blocks into one highly integrated chip will furthermore reduce the system complexity due to a reduced number of required external components and hence reduced system cost. The more compact system architecture will furthermore be appreciated for example in in-vivo endoscopy. Thirdly, the separation of light launch, Raman signal generation and light extraction can be used to optimize each functional block to its specific task (for example light extraction as opposed to maximum SERS enhancement).

Finally, compared to topologies that rely on colloidal crystals, the proposed fabrication method that defines the pattern by lithographic means as opposed to self-assembly promises greater reproducibility and increased yield. The scalability of the novel anisotropic wet and deep Silicon etching fabrication processes for the generation of SERS substrates provides a cost-effective method of mass producing identical SERS substrates while still maintaining high reproducibility of signals across different experiments; different substrates on the same wafer; and/or different substrates on different wafers.

BRIEF DESCRIPTION OF THE DRAWINGS

The system will now be described in detail with reference to the accompanying drawings, in which:

[FIG. 1(a) illustrates a photonic crystal (PC) area that exhibits a continuous metallodielectric film on its surface and wells. FIG. 1(c) shows a structure in which the SERS active region is located on top of an air cavity. FIGS. 1(b) and 1(d) show structures corresponding to FIGS. 1(a) and 1(c), respectively, in which only the wells are coated with a metallodielectric layer. FIG. 1(e) depicts another embodiment illustrating a photonic crystal (PC) comprising of inverted pyramidal wells while in FIG. 1(g) truncated inverted pyramidal wells are also shown. FIGS. 1(f) and 1(h) describe inverted pyramids and truncated inverted pyramids in which only the wells are metal coated. FIGS. 1(i) and 1(k) depict structures with inverted pyramid structures with cylindrical holes extending from the apex of the pyramid into the substrate, additionally the metal coating is continuous across all the structure and the metal coating resides only in the wells respectively.]

FIG. 2 shows an example of an embodiment in which the multilayer dielectric structure into which the PC SERS region is defined forms a waveguide structure;

FIG. 3 shows an embodiment in which the multilayer dielectric structure into which the PC SERS region is defined forms a multilayer mirror structure;

FIG. 4 displays four example embodiments of structures that are designed for receiving or extracting optical radiation;

In FIG. 8B(l) illustrates the structure arising from combining an anisotropic wet etch and a highly anisotropic anodic etch;

FIG. 9 schematically illustrates the method of obtaining a Raman signal from an analyte under investigation;

FIG. 14A shows the theoretical reflectance simulation result for the surface of a metal-coated inverted pyramidal PC-SERS structure, while FIG. 14B illustrates the properties and geometry of this structure;

FIGS. 15A, B, C and D relate to the effect of surface corrugations. FIG. 15A shows the simulated localization of a TM field and the associated surface and localized plasmons in the structure of FIG. 14B with a smooth surface. FIG. 15B shows TM field localization associated with rough corrugations in a flat surface. FIG. 15C shows TM field localization in an inverted pyramid with rough surface corrugations due to metal deposition, while

FIG. 16A illustrates the experimental Raman data from a metal coated air rod PC-SERS substrate.

FIGS. 17A, B and C relate to the effect of surface corrugations. FIG. 17A is a high resolution Field Emission Gun-SEM micrograph of the inverted pyramid PC-SERS structure of FIG. 16B showing the surface roughness. FIG. 17B shows the experimental SERS signal (lacking the characteristic Raman lines) from a Benezenethiol monolayer on a rough corrugated flat metal substrate (the SEM insert shows the surface roughness), while FIG. 17C shows a 2D plot of the measured dispersion characteristics of the inverted pyramid PC-SERS structure;

FIG. 18D demonstrates the TM polarised field localisation in an inverted pyramid structure and the associated surface and localized plasmons;

FIG. 18E shows the predicted field distribution based on a simple model of propagating surface plasmons confined in the inverted pyramid;

FIG. 18F shows the variation in the SERS signal from a monolayer coverage of 4-aminothiophenol as a function of the inverted pyramid diameter; and, FIG. 19 Illustrates the plan view of a fabrication-tolerant and wavelength-insensitive metallodielectric photonic crystal structure designed to possess many different localised plasmon resonances and a broad surface plasmon resonance allowing the SERS incident laser spot size to cover many unit elements and hence providing more efficient input laser coupling as well as more reproducible SERS output signal irrespective of the wavelength of operation.

DETAILED DESCRIPTION

SERS Active Platform

One aspect of the present system is a planar platform for receiving optical radiation from an optical source, as will now be described.

Figure 1:
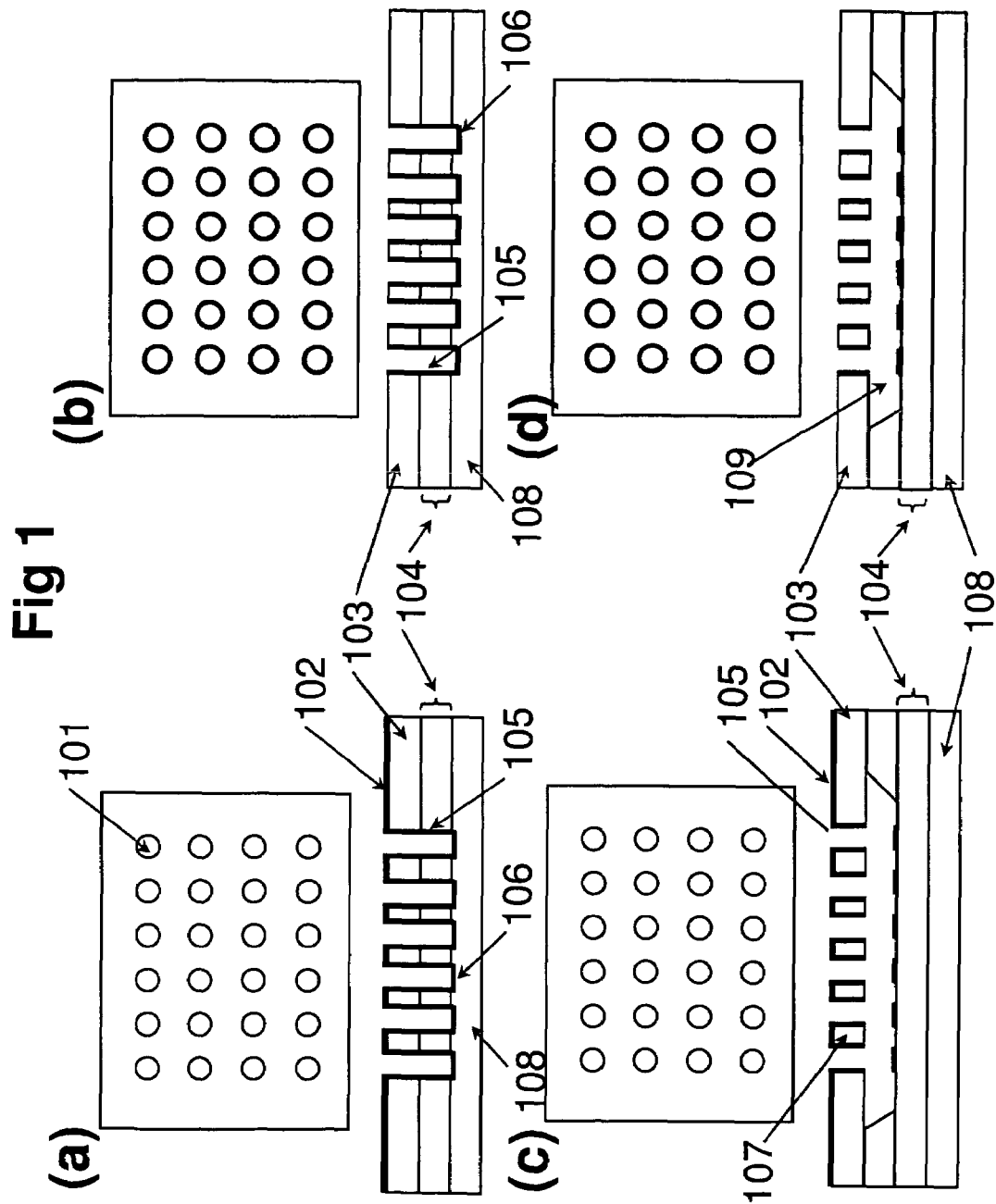
FIGS. 1(a)-(k) depict ten exemplary embodiments.

In a first embodiment of the platform depicted in FIG. 1(*a*), the platform comprises a dielectric layer with a predefined surface modulation (patterning) coated with a continuous metallodielectric coating 102, 105, 106.

The surface modulation is achieved through the definition of a 2D periodic array of holes or wells 101 embedded in the otherwise planar dielectric surface 103. Topologies of the 2D periodic lattice structure can include, but are not limited to square, triangular, and rectangular lattice geometries. The array of holes can also be arranged to form a graded or doubly graded 2D photonic crystal lattice, a quasiperiodic photonic crystal, or a lattice structure with one or more defects. If the array of holes is arranged in a regular lattice, it will feature a typical lattice pitch. In a preferred embodiment, the holes or wells 202 will have the shape of cylindrical air rods (pores) with hole diameter 206 and height 203, as shown in FIG. 2.

In another embodiment, the holes or wells 110 have the shape of inverted pyramids (FIG. 1(*e*)) or inverted truncated pyramids 111 (FIG. 1(*g*)) with square base lengths 115 and height 116. The well is not restricted to inverted pyramids and may take the form of an inverted polyhedron.

In another preferred embodiment (FIGS. 1(*i*) and 1(*k*)) the holes or wells may take a hybrid shape of an inverted pyramid (top view 118) combined with an extended deep cylindrical air rod. The high aspect ratio air rods extend from the apex of the inverted pyramid into the underlying substrate.

The structure is coated with a metallic or metallodielectric layer that can contain several metallic and dielectric films. In the simplest implementation the layer just a single metallic film. Each layer, labelled as j, can be of a different material and will generally have a different thickness 204 for the top 102, 205 for the hole (well) sidewalls 105, and 207 for the hole (well) floors 106 of the structure, respectively. In a preferred embodiment, the thicknesses of the metal layers are chosen to be optically thin. The metal can be selected from, but is not limited to, the following group of metals: gold, platinum, silver, copper, palladium, cobalt, and nickel and iron.

In order to improve the adhesion of the metal to the dielectric surface, an adhesive layer 208 such as Chromium or a monolayer of Mercapto-propyl-trimethoxysilane ('mercaptosilane') can be deposited on top of any dielectric material prior to depositing a metal layer, as shown in FIG. 2.

In one example of an embodiment, the modulated dielectric surface is coated by a continuous metallic film, which covers the top surface as well as the sidewalls and bottoms of the holes, as depicted in FIG. 1(*a*). In another embodiment, depicted in FIG. 1(*b*), only the holes (wells) are coated with a metal film 105 and 106 with no metal film present at the top surface of the structure.

Figure 11:
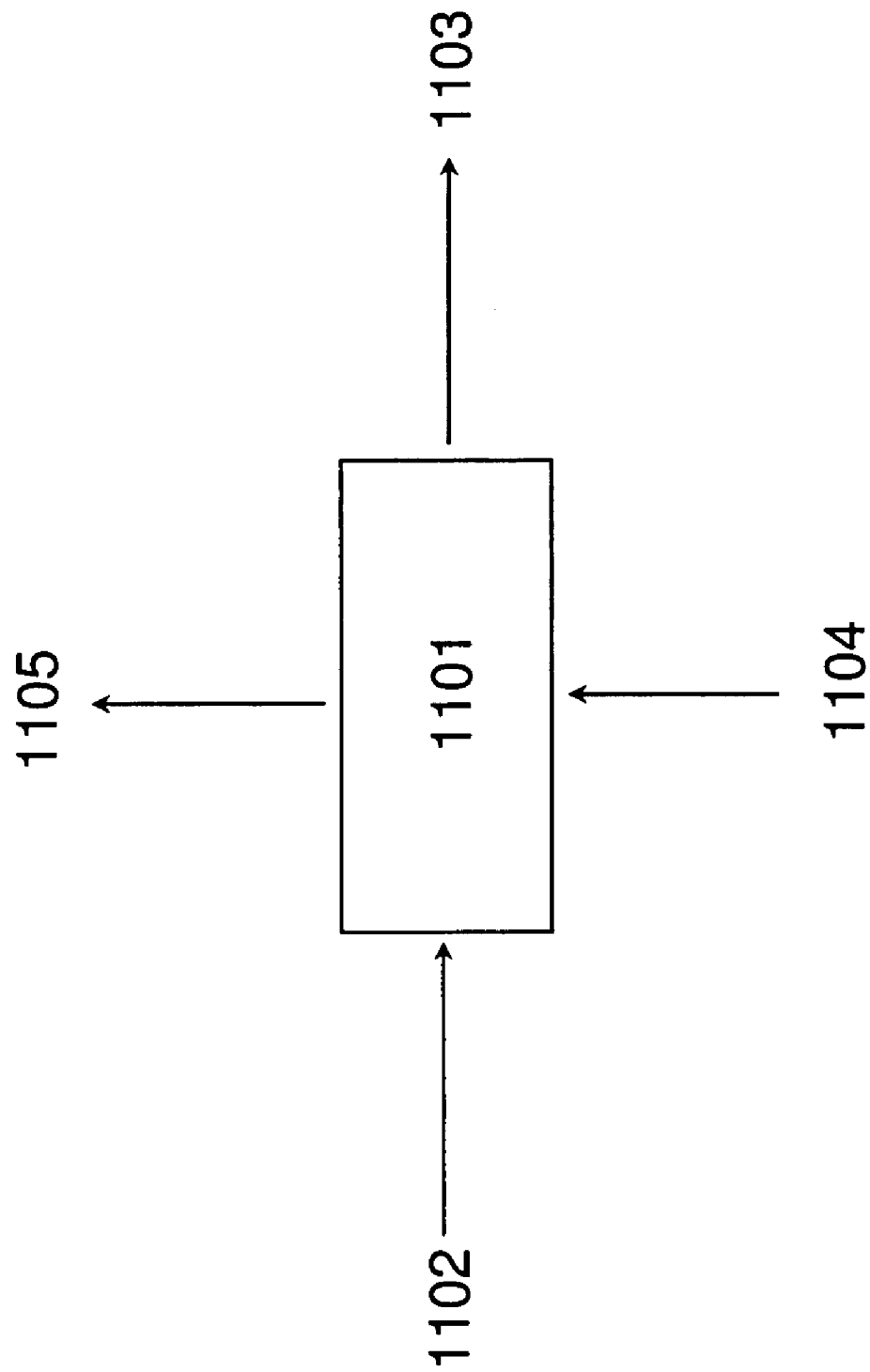
FIG. 11 schematically illustrates a setup in which the analyte is continuously flowing through the platform during the measurement.

In yet another embodiment, the metal-coated dielectric is arranged in a membrane configuration as depicted in FIG. 1(*c*) for the case of metal covering both the top surface and the sidewalls. In this configuration, the metal-coated dielectric lattice is undercut by an air region 109, often referred to as air bridge or membrane structure. The PC region is mechanically connected by the dielectric areas 107 surrounding the holes 101. The deposited metallodielectric layer will also be selectively deposited at the bottom of the air cavity. As schematically depicted in FIG. 11, in the membrane configuration, the analyte can flow through the platform 1101 from one side 1102 to the other 1103 during the measurement in which optical radiation 1104 is for example incident from the top and the Raman signal 1105 emerging from the platform is detected for example in the reflection regime. This configuration gives the experimentalist the freedom to mechanically control the adsorption properties (such as chemical binding energy and adsorption efficiency) of the analyte molecules to the SERS active region. Optically, any waveguide modes propagating in the core of the structure experience a symmetrical cladding and buffer material (namely air) and hence symmetrical modes can be set up. This can provide means of optically probing and exciting analyte molecules 211 located above and below the air bridge structure. FIG. 1(*d*) depicts yet another embodiment similar to the previous configuration, in which only the sidewalls 105 of the holes and selected regions at the bottom of the air cavity are coated by a metallodielectric layer.

In the case of FIGS. 1(*e*), 1(*g*) and 1(*i*), a continuous metallic film 117 extends along the angled facets 112 and the bottom surface 113 (where present) of the inverted pyramids (FIG. 1(*e*)), inverted truncated pyramids (FIG. 1(*g*)) and hybrid inverted pyramid-rod structures (high-aspect ratio structure, as depicted by FIG. 1(*i*)).

In other embodiments, depicted in FIGS. 1(*f*), 1(*h*), and 1(*k*), only the inverted pyramids (FIG. 1(*f*)), inverted truncated pyramids (FIG. 1(*h*)) and hybrid inverted pyramid-rod structures (FIG. 1(*k*)) are coated with a metal film 106. As illustrated in FIGS. 1(*f*), 1(*h*) and 1(*k*), the metal film 117 only resides along the angled facets and is absent from the top surface of the structure (compare to FIGS. 1(*e*), 1(*g*) and 1(*i*) respectively).

Furthermore, in all embodiments, the substrate consists of multilayers 104 of dielectric material, in its simplest implementation just being a single dielectric layer. In the examples of FIGS. 1(*e*)-(*k*), the single dielectric layer comprises of a single crystal substrate such as, but not restricted to, Silicon and the angled facets 112 are formed along the crystal planes. The single crystal substrate is required to provide a simplified method of manufacture whereby anisotropic wet etching can follow the crystal planes and inverted polyhedra can be formed.

Other implementations, include a planar waveguide structure 212 cladded by a substrate 108 and a cladding 103 as depicted in FIG. 2 and a distributed Bragg reflector 301 as depicted in FIG. 3. The dielectric layers can have a residual distance 210 to the bottom of the holes (wells) or can be partially or fully perforated by the same. In a preferred embodiment of the planar waveguide 212, its thickness 209 and distance 210 from the floor of the holes (wells) is chosen such that it can vertically confine light of a preselected wavelength $\lambda_i$ while still providing optimal coupling to the SPP. In a preferred embodiment of the planar DBR mirror, the thicknesses of the layers forming the mirror are chosen such that the center of the stop band coincides with the preselected wavelength $\lambda_i$ of the incident light. In another embodiment, the DBR mirror can be designed such that the reflective region of the structure coincides with the most critical wavelength region of the generated Raman signal, hence providing an increased SNR. The multilayer structure can also be composed to form an omnidirectional reflector (ODR).

When the wavelength $\lambda_i$ of the incident light corresponds to a frequency close to the plasma frequency $$\omega_p = \sqrt{\frac{4\pi n q^2}{m^*}} \tag{1}$$

of the surface metal, conduction electrons in the metal surface can be excited into a surface electronic excited state called surface plasmon which will be predominantly localized at defects of the metal surface. Here, n denotes the electron density, q the electron charge, and m* the effective mass. In the absence of a periodic modulation of the metallic surface, the dispersion relation of the surface plasmons is given by $$k_{SP} = k_0 \sqrt{\frac{\varepsilon_D \varepsilon_M}{\varepsilon_D + \varepsilon_M}} \tag{2}$$

where $\lambda_M$ is the frequency dependent complex dielectric constant of the metal, $\lambda_D$ is the frequency dependent complex dielectric constant of the dielectric, $k_{SP}$ is the complex wave vector of the surface plasmons, and $k_0$ is the wave vector of the incident optical radiation.

The light excites localized surface plasmons (SPs) at defects within the structure, but can also excite surface plasmons polaritons (SPPs) at the air-metal interface if, as in our proposed topologies, certain conditions are met. Namely, a periodic modulation of the complex dielectric constant of the metal is introduced and the angle of the incident light is selected such that the following phase matching condition is satisfied:

$$k_{SPP} = \pm k_0 \sin \theta \pm mQ \tag{3}$$

where $Q = \pi/\Lambda$ is the reciprocal lattice vector of the periodically corrugated metal surface with corrugation period $\Lambda$ in a particular lattice direction.

If the modulation period $\Lambda$ equals half the wavelength $\lambda_{SPP}$ of the surface plasmon polaritons $$\Lambda = \frac{\lambda_{SPP}}{2}, \tag{4}$$

the periodic wave functions of the surface plasmon polaritons can form standing waves on the surface of the metal, leading to a perturbation of the SPP dispersion (2) through the formation of a SPP band gap in which no surface plasmon polariton states are allowed to exist. This phenomenon is equivalent to the formation of a photonic band gap in photonic band gap structures or to the formation of band gaps for electrons in solids.

Similarly, SPPs can be excited inside the holes that can in turn couple onto the SPPs at the top surface.

In the following mathematical expressions, the Electric ($E_r$, $E_\theta$, $E_z$) and Magnetic fields ($H_r$, $H_\theta$, $H_z$) solved in cylindrical coordinates (r, θ, z) for the surface plasmon dispersion of a single metal cylinder of finite thickness are presented:

$$E_r = \left(\frac{ik_z}{k_j} a_n^j f_n^{j'}(k_j r) - \frac{\omega n}{k_j^2 r} b_n^j f_n^j(k_j r)\right) S_n \tag{5}$$

$$E_\theta = \left(-\frac{nk_z}{k_j^2 r} a_n^j f_n^j(k_j r) + \frac{i\omega}{k_j} b_n^j f_n^{j'}(k_j r)\right) S_n$$

$$E_z = a_n^j f_n^j(k_j r) S_n$$

$$H_r = \left(\frac{n\varepsilon_j \omega}{k_j^2 r} a_n^j f_n^j(k_j r) + \frac{ik_z}{k_j} b_n^j f_n^{j'}(k_j r)\right) S_n$$

$$H_\theta = \left(\frac{i\varepsilon_j \omega}{k_j} a_n^j f_n^{j'}(k_j r) - \frac{nk_z}{k_j^2 r} b_n^j f_n^j(k_j r)\right) S_n$$

$$H_z = b_n^j f_n^j(k_j r) S_n$$

where $\varepsilon_j = \varepsilon_0 n_j^2$, $\varepsilon_j$ is the dielectric permittivity of the medium j, $n_j$ is the refractive index of the medium j, $\varepsilon_0$ is the dielectric permittivity in a vacuum, the exponential factor $S_n = e^{in\theta + ik_z z - i\omega t}$, the radial component of the wave vector in the $j^{th}$ layer is $$k_j^2 = \left(\frac{2\pi}{\lambda}\right) \sqrt{n_j^2 - n_{effective}^2},$$

and $n_{effective}$ is the effective index of the plasmon mode.

The cylindrical structure comprises of three layers (j=3), where the first radial medium is the core region (j=0) of the cylinder and is typically air. The second medium is composed of the metal (j=1), and finally the third medium (j=3) composed of a dielectric material, namely the cladding structure.

The general solution for this set of equations is composed of a Bessel function of the I and K form, but the appropriate boundary conditions must also be applied, namely that the tangential components of the E and the H are continuous at the inner and outer cylinder radii of the metal film. Matching the field components at the boundaries results in a system of linear equations for the coefficients $a_n^j$ and $b_n^j$. A nontrivial transcendental equation results having roots that yield the surface plasmon dispersion relations (derived from ($n_{effective}$). This equation is numerically solved by a method such as a bisection and Newton Raphson method or preferable a more accurate method such as the Augmented Principle Method.

Furthermore, if the holes are brought into close proximity, the evanescent field that extends into the dielectric can couple from one hole to its neighbour, hence independently forming a band structure that can exhibit a band gap even in the absence of a connected metal top surface.

For the modelling of SP modes in inverted pyramidal structures an Auxilliary Differential Equation—Finite Difference Time Domain (ADE-FDTD) method is used. The dielectric permittivities (∈) of the metal layers are approximated by the use of sixth order-term Lorentzian functions as shown below, $$\varepsilon(\omega) = \sum_{j=1}^{6} \frac{f_j \omega_p^2}{\omega_j^2 - \omega^2 + j\omega \Gamma_j} \quad (6)$$

where j is the number of oscillators where each possesses a strength of $f_j$ and frequency $\omega_j$, while $\omega_P$ is the metal plasma frequency.

Figures 14A, 14B:
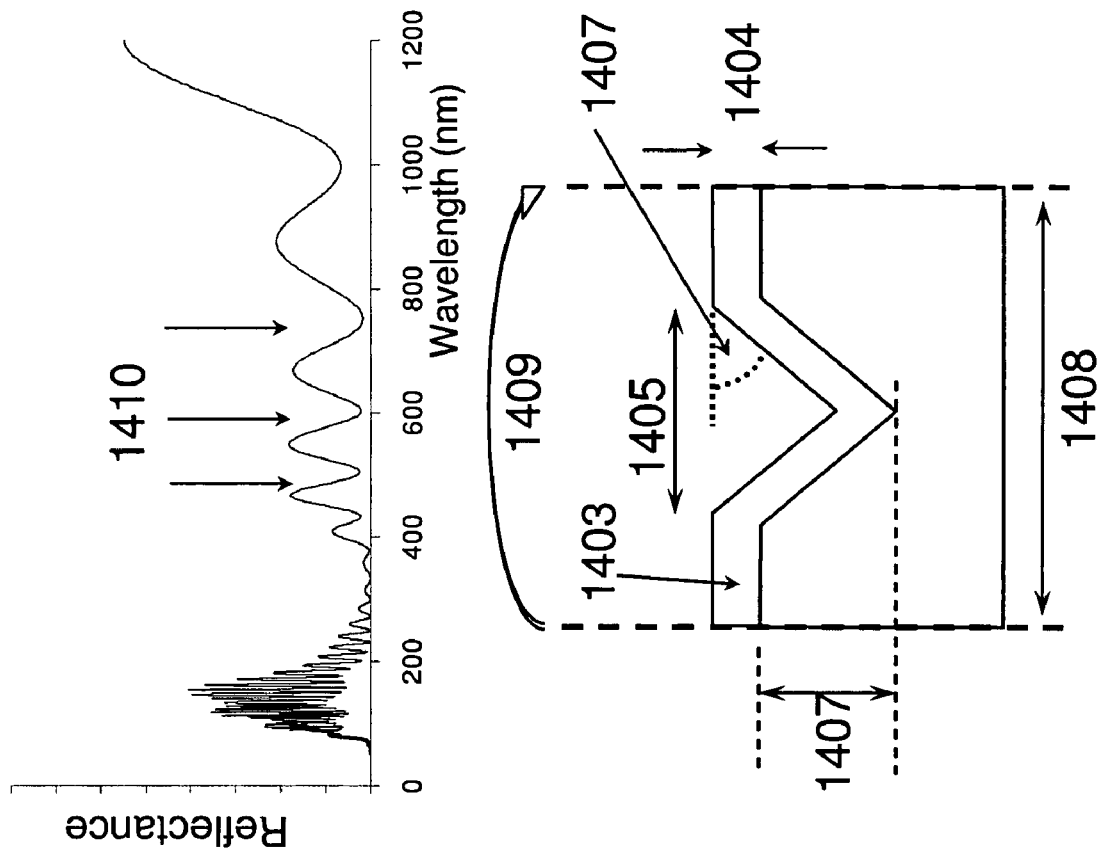

A normally incident TE polarised Gaussian packet is reflected off the surface of the structure and the reflectivity power versus wavelength is collected. An example TE polarised light simulation is plotted in FIG. 14 where the reflected power 1401 is plotted versus wavelength 1402. The simulated structure geometry is highlighted in FIG. 14B. The periodicity of the pyramid 1409 is selected as 2 mm while the pyramid size 1405 is varied from 0.5 mm to 1.5 mm, the angle 1407 is selected as 45° and the thickness 1404 of the selected Gold metal is 0.3 mm. Several resonances are visible on the plot. It is noted that regions where dips in the reflection occur, 1410, indicate regions where surface plasmons are coupled into, this results in the light not being reflected back. These are regions of most importance and structures are designed so that the SPP resonance coupling is matched with the desired input wavelength.

Figure 18A:
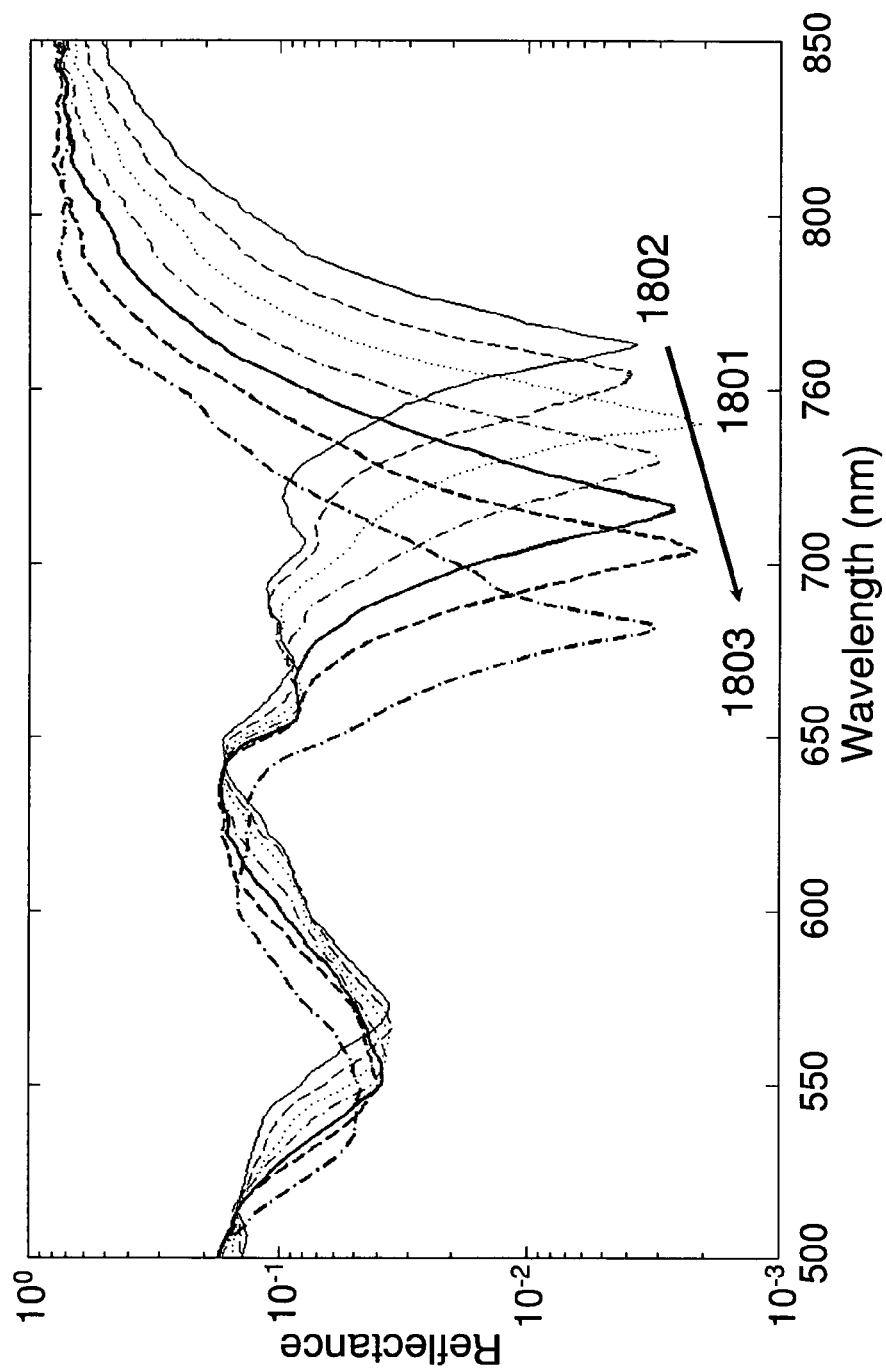
FIG. 18A shows experimental reflectivity plots at normal incidence demonstrating the variation in the plasmon resonance for different pyramid size structures.
Figure 18B:
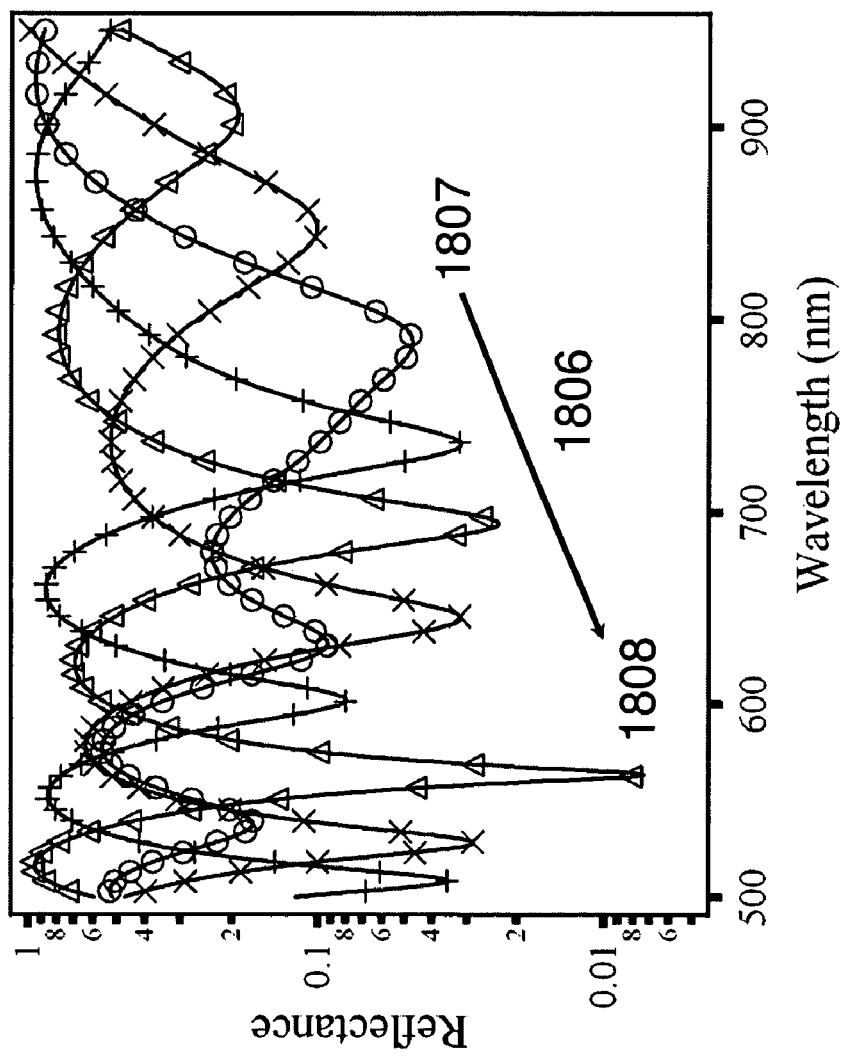
FIG. 18B shows theoretically modelled reflectivity plots at normal incidence demonstrating the variation in the plasmon resonance for different pyramid size structures with a fixed pyramid pitch.

FIG. 18A shows the experimental reflectivity spectra for a range of plasmonic bandstructure substrates of the type shown in FIG. 17A. The normalised normal incidence reflectivity is plotted against wavelength in nanometers. The pitch of the plasmonic bandstructure substrates is fixed at 2 microns while the inverted pyramidal diameter is varied from 0.9325 μm to 0.7825 μm. Over this range, the plasmon resonance is seen to shift to higher energy (shown as a wavelength shift 1801 from long 1802 to short 1803 wavelength). This is theoretically verified using the 2D ADE-FDTD in 18B, where the plasmon resonance also blue shifts 1806 when the inverted pyramid diameter varies from 1.25 μm to 1.00 μm, resulting in the resonance wavelength shift from 1807 to 1808.

Figure 18C:
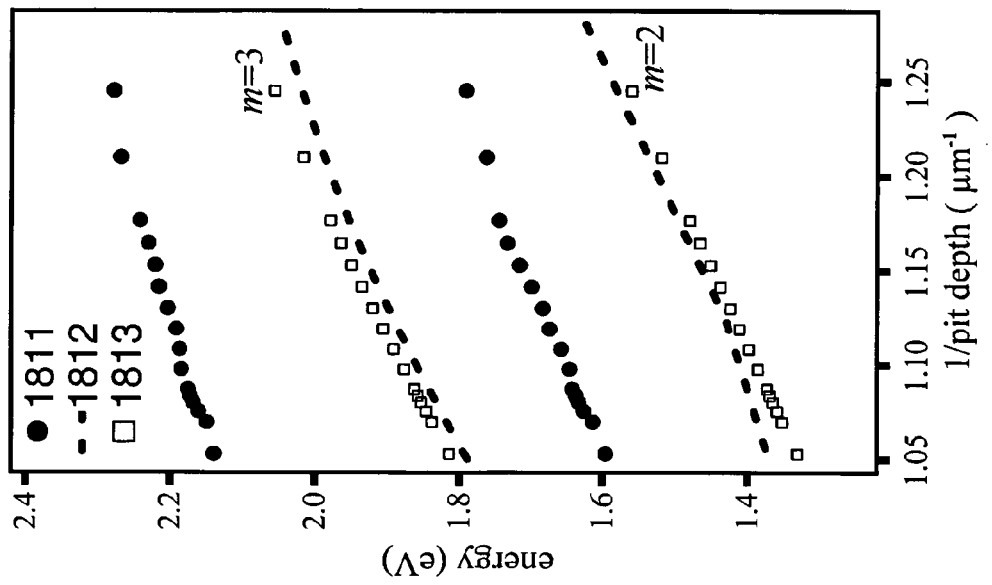
FIG. 18C is a plot of energy for the first few confined Surface Plasmon (SP) states versus pit depth. Results are shown for the simple theoretically model, the full Finite-Difference Time-Domain (FDTD) modeling and real experiments.

In addition, as shown in FIG. 18C, the plasmon energies in electron-volts are extracted from the FDTD simulation (shown as broken lines 1812) and the experiment (shown as solid circles 1811) and plotted against inverse pyramid hole depth. The second (m=2) and third (m=3) order modes from both theory and experiment are highlighted and both possess an identical energy spacing and same dependence on pit depth. The visible shift between experiment and theory is attributed to the 2D simulations modelling surface plasmons on V-groove type structures (which are effective cross-sections of inverted pyramidal structures) while experiments were performed on 3D inverted pyramids.

An alternative simple intuitive model is also proposed that is based on confinement of propagating surface plasmon polaritons (SPP) on the sides of the inverted pyramid. The model assumes that the top of the inverted polyhedra acts as an infinite reflecting barrier for surface plasmons and the sharp inverted pit bottom transmits surface plasmons. Using these assumptions, a simple model can be derived that predicts the resonant plasmon energies as follows:

$$\hbar \omega = \frac{\pi \hbar c}{n_{SPP}} \cdot \frac{\cos \alpha}{d} \cdot \left( m + \frac{1}{2} \right) \quad (7)$$

where $n_{SPP}$ is the effective refractive index of the SPP modes on flat gold, ω being the angular frequency of the incident light, m the order of the plasmon mode, d is the inverted pyramid depth and α being the inclination angle of pyramid face to the normal (in this case being 35.3 degrees), while h being the reduced Planck's constant.

The first two modes of the simple model are superimposed on FIG. 18C (open squares 1813) and are seen to match extremely well the extracted plasmon resonances from the FDTD model. FIG. 18D demonstrates the modelled TM polarised field localisation in an inverted pyramid structure and the associated surface and localized plasmons. While in FIG. 18E the intuitive predicted field distribution is sketched based on the simple model of propagating surface plasmons confined in the inverted pyramid. The localised plasmons can thus be approximated by delocalised surface plasmons travelling up and down the sidewalls of the inverted pit. This provides plasmon modes able to form resonant standing waves between the nodes at the top rim of the pits.

The ADE-FDTD method can also provide a means of quantifying the time averaged square of the incident laser pump field, $<E_{LASER}^2>$, localised along the surface of the PC-SERS structure as well as the localised time averaged square of the Raman field, $<E_{RAMAN}^2>$. Using this data, an effective Figure Of Merit (FOM) for the level of enhancement of the SERS due to the localisation of the field may be computed, when defined as FOM=$<E_{LASER}^2><E_{RAMAN}^2>$. Using the FOM provides a means of predicting the SERS enhancement and subsequently the control of reproducibility across the surfaces.

It is known in the prior art that small-scale roughness (of the order of 10 nm-100 nm) can play a fundamental part in the generation of SERS. However, roughness is also inherent in most metal deposition processes. For example, depending on the fabrication process selected, the metallodielectric layer may comprise of metallodielectric microcolumnar random corrugations. This microcolumnar roughness can also be modelled using the ADE-FDTD method. This technique provides a method of modelling the SERS FOM and localization properties associated with both the surface roughness and the PC-SERS structure.

FIG. 15A shows the simulated localization of the time-averaged TM polarised laser pump wavelength at 785 nm incident on an inverted pyramid PC-SERS structure with a smooth surface. The structure comprises a Silicon Oxide substrate 1514, a deposited metal layer 1513 of thickness 300 nm, and a top air region 1515. The results are computed for a structure comprising inverted pyramids arranged in a square array on a 1 micron pitch and with a pyramid size of 650 nm. The strong localised plasmons 1512 are clearly visible, as well as weaker surface plasmons 1511.

The corresponding results for a flat but corrugated gold metal surface are shown in FIG. 15B. As a first order approximation, the corrugated flat gold metal structure is modelled as a nanoscale periodic structure of microcolumnar air cavities with a roughness pitch of 70 nm and microcolumn diameter of 50 nm and depth 100 nm. It is known that microcolumnar structures can provide large SERS FOMs due to the strong Mie-like plasmon localizations around single microcolumns in the roughness, as indicated by 1516.

Figure 15C:
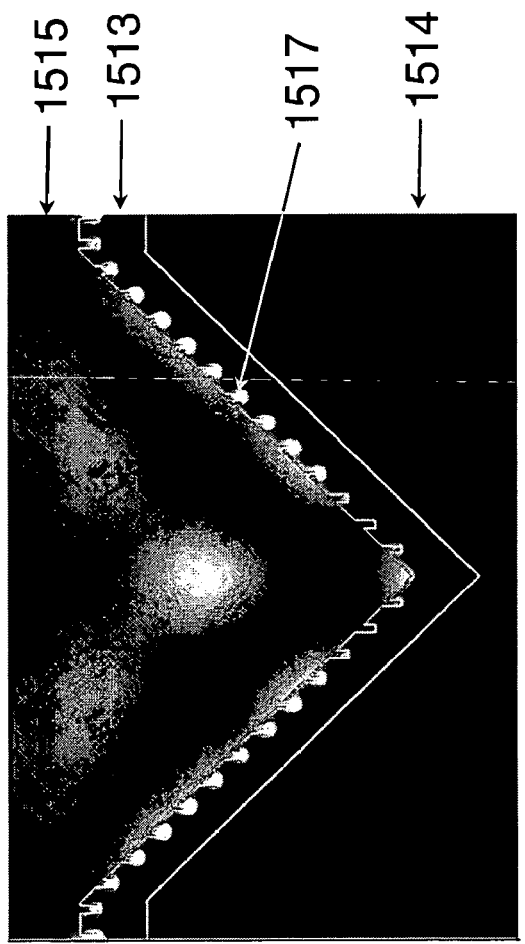
Figure 15D:
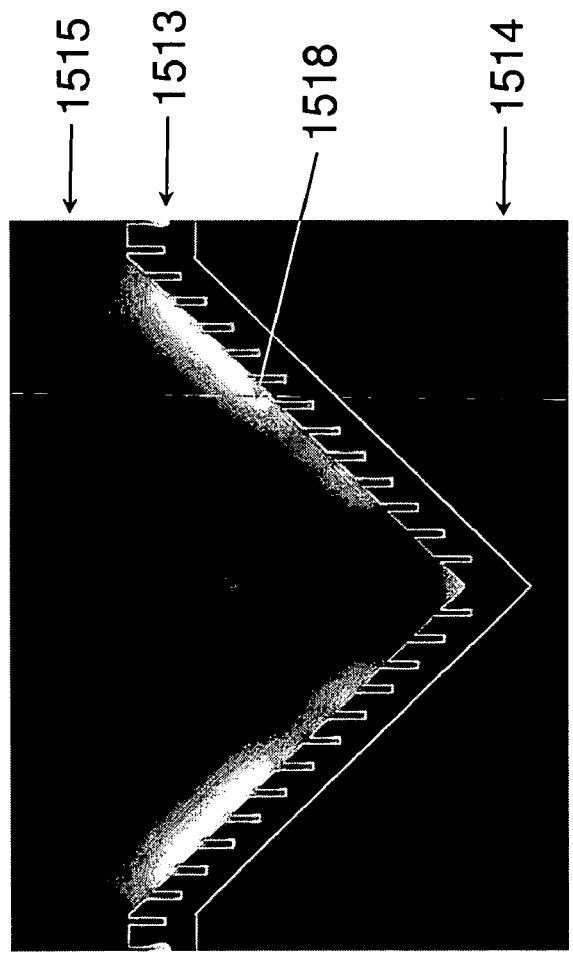
FIG. 15D shows TM field localization in an optimally designed pyramid with rough surface corrugations.

FIG. 15C shows the localisation of the electromagnetic field when rough corrugations are superimposed on the PC-SERS structure of FIG. 5A. The localisation of incident TM polarised 785 nm laser light is mainly in the rough corrugations (small scale Mie-like resonances) 1517, but partly forms surface plasmons and localised plasmons (due to the large scale plasmonic bandstructure). However, in a preferred embodiment, the parameters of Photonic Crystal SERS region and the physical properties of the metal layer are selected so that surface and localised plasmons (1518) that are independent of the small-scale rough corrugations but dependent on the large scale plasmonic bandstructure features can dominate. The simulated results for such an optimized structure are shown in FIG. 15D. In the specific examples shown, the microcolumnar rough corrugations are varied from 25 nm depth for the structure of FIG. 15C (providing large small-scale mie-like plasmon resonance) to a depth of 100 nm for the structure of FIG. 15D. This of type of optimized design ensures high reproducibility from the SERS substrate, irrespective of the corrugation roughness properties.

The photonic crystal lattice parameters can be chosen to extend the lifetime of the surface plasmons to increase the chance of coupling to the analyte molecules and hence increase the sensitivity of the measurement. Furthermore, upon an appropriate change of the array pattern, the angular direction of the emitted Raman signal may be modified.

If an analyte 211 is brought in close proximity to the metallodielectric layer, energy can be coupled from the various plasmonic states to the analyte molecules to excite its various vibrational modes and accordingly result in an enhancement of the Raman signal: the extraordinary large EM field associated with the SPP can enhance the molecule's vibrational modes, predominantly those normal to the metal surface. The molecules relax and either emit EM radiation or pass energy back to the plasmonic surface states that mediate the emission of the Raman signal.

The SERS enhancement largely depends on the distance of the molecules from the metal surface. Two mechanisms contribute to the SERS enhancement: an electromagnetic (EM) contribution and a chemical contribution.

Depending on the distance of the adsorbate molecule to the metal surface, the EM or chemical contribution will become more pronounced. Generally, the closer the binding of the adsorbate to the metal to form a adsorbate-molecule complex, the stronger the chemical effects will be while still being dominated by the EM effects.

Additionally, the structure can also be designed to vary the penetration depth of the evanescent field into the air cavities and hence provide a means of tailoring the detection to be sensitive to adsorbates further away from the metallodielectric surface. This may be achieved by varying the photonic crystal lattice parameters as well as the thickness of the metallodielectric layer. The resulting structure can be beneficial for the detection of large analyte molecules as well as biological material such as cells, bacteria or viruses, where large feature dimensions are to be detected.

The long-range contribution is believed to be due to resonant excitation of the SPPs by the incident light wave as described above. However, if the adsorbate is in contact with the metal surface, it forms a metal-adsorbate complex such that the short-range contribution to the enhancement can no linger be ignored. It is believed to be due to a modification of the ground-state electronic charge density distribution (as a result of a charge transfer (CT) exciton) and new electronic excitation spectrum.

As yet, the charge transfer (CT) mechanism is not entirely understood. Two main approaches are considered: a CT mechanism similar to the resonant Raman mechanism, and a non-radiative CT mechanism. It is believed that depending on the strength of the adsorption of the molecule to the metal surface, either of the two models dominates the short-range enhancement mechanism.

The analyte molecules can be in close proximity to the metal at the bottom or the sidewalls of the holes, the aperture of the holes, to a defect region within the PC lattice, or, if applicable, to the metallodielectric-coated top surface of the structure.

Regardless of the details of the particular mechanisms, the quintessential role of SPPs in the enhancement of vibrational modes of molecules adsorbed at a metal surface is undisputed. Naturally, it becomes apparent that a redistribution of the SPP states has great potential to fundamentally increase the SERS effect.

The energetic difference between the incident signal and the Raman scattered light is equivalent to the vibrational energy of the adsorbate molecule and can be expressed by the Raman shift $\Delta k$ $$\Delta k = \frac{1}{\lambda_i} + \frac{1}{\lambda_{scatt}} \tag{8}$$

Since the Raman shift depends on the vibrational modes of the adsorbate molecule, it is characteristic to the molecule and can therefore serve as a fingerprint of the analyte under investigation. The Raman shifted signal is collected either out of the plane of the platform or in the plane of the waveguide structure.

Analytes can include chemical warfare agents, pesticides, urea, lactic acid, pollutants, ascorbate, and glucose, or biomolecules such as proteins, lipids, nucleic acids (bacterial and viral DNA, RNA, PNA and others).

The platforms include regions for receiving and extracting optical radiation. These regions can be selected from, but are not limited to, the following group of metallic, metal-coated dielectric, or dielectric photonic band structures: gratings, graded gratings, periodic two-dimensional photonics crystals, graded or doubly graded two-dimensional photonic crystals, quasiperiodic two-dimensional photonic crystals. Regular arrangements can include, but are not limited to square, triangular, and rectangular geometries. The filling fraction of the air rods or air slots and their respective etch depth can be selected to facilitate optimum coupling of light to or from the in-plane wavevectors of the underlying multilayer structure that can transport the light to and from the platform that generates the Raman signal. Exemplary embodiments of such structures are depicted in FIG. 4.

FIG. 4(a) shows a grating structure 401 with lattice parameters (grating pitch, groove width, groove depth) chosen such that light can optimally couple into the in-plane wavevectors of the underlying multilayer structure. FIG. 4(b) illustrates a second exemplary embodiment for receiving or extracting EM radiation, in this case a 2D photonic band structure device 404 composed of a rectangular array of air rods. FIG. 4(c) shows a photonic crystal 405 with a quasiperiodic lattice topology which can be used to produce a modified emission pattern of the optical radiation. FIG. 4(d) depicts a fourth exemplary embodiment of a structure for receiving or extracting optical radiation, in this case a cleaved facet 408 of the device. A rib or ridge structure 407 can be directed to the end of the facet. The waveguide can furthermore be tapered to provide mode matching to an external optical fiber for launch (402) or collection (403) of EM waves.

FIG. 4(*a*) represents a preferred embodiment for the realization of a structure for receiving optical radiation while FIG. 4(*c*) represents a preferred embodiment of a structure for extracting optical radiation.

Figure 5:
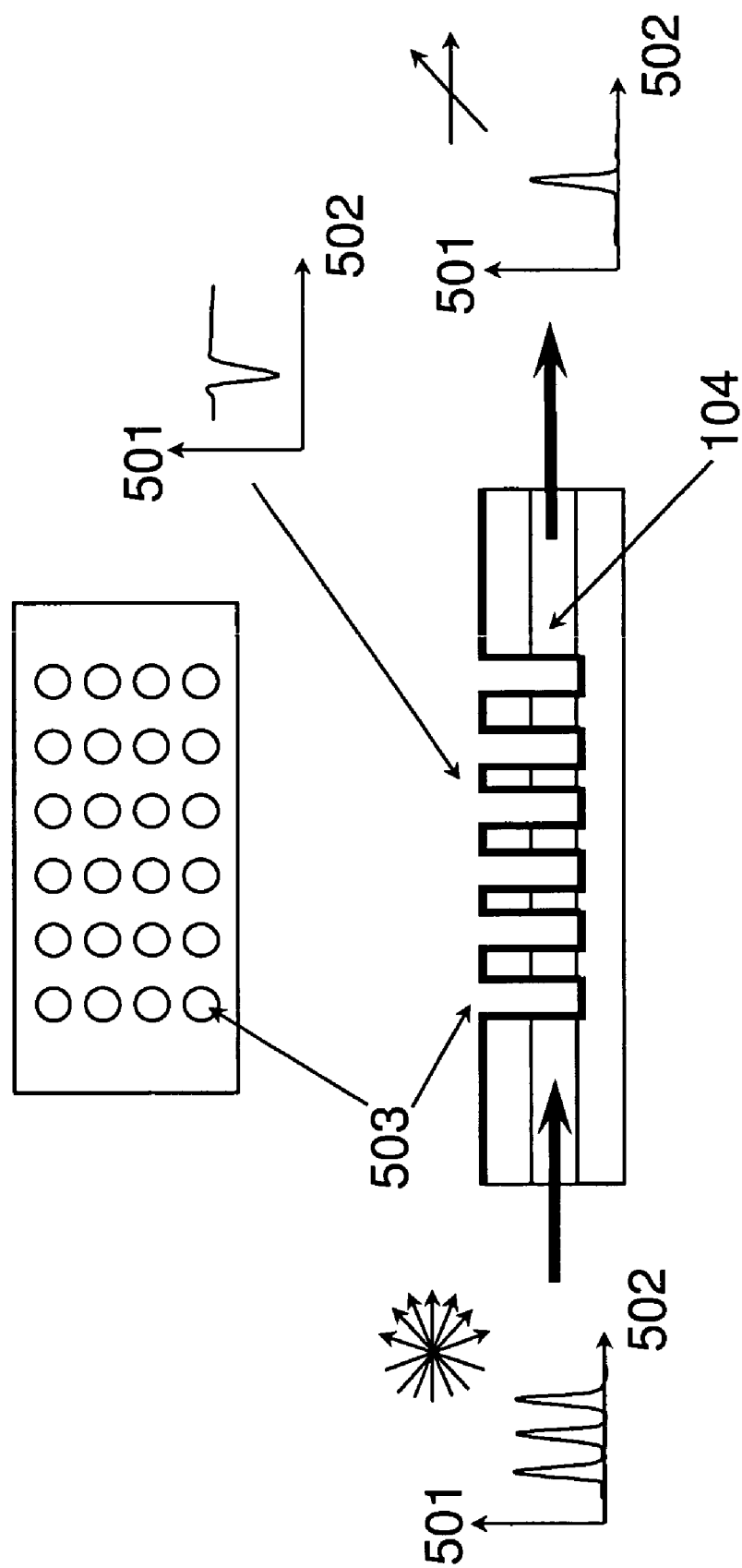
FIG. 5 displays a schematic drawing of a structure that is designed for pre- or postprocessing of optical radiation.

The platform can further include a structure 503 for pre- and/or postprocessing of optical radiation. In a preferred embodiment, the wells are completely penetrating a planar waveguide structure located underneath the platform surface as illustrated in FIG. 5.

The topology of the photonic band structure (lattice period, air hole diameter and depth) is chosen such that the structure meets a pre-selected functionality, in which an incident optical signal of intensity 501 at wavelength 502 experiences some form of optical manipulation. Examples include the following group of processes: spectral filtering, polarization filtering, optical time delay, beam steering, diffraction, and spatial resolution of different photon energies. Infiltration of the pores with a tunable material such as nematic liquid crystal or electrically modulated nonlinear material and application of electrodes on the top and bottom of the substrate facilitates an electronic alteration of the respective function. For example, a modification of the applied voltage results in a polarization-dependent shift of the photonic band gap of the photonic crystal (PC) section. This may be used to band stop or band pass light of a particular polarization state, and thus serve as an electronically controllable polarization filter, or to pass or not pass light of a certain frequency range, thus serving as an electronically controllable wavelength filter.

A waveguide structure 212 can transport energy from one functional block 601, 602, 604, 605 to an adjacent functional block. The refractive index of the stack, the thickness 209 of the waveguide core, and its distance (the sum of distances 203 and 210) to the top surface are chosen such that out-of-plane radiative losses are minimal. This is achieved by solving the waveguide dispersion relations and selecting guided lossless modes. Additionally, the waveguide mode can be confined laterally using one of several mechanisms. One example is resonant coupling of optical modes, as provided by photonic crystal line defects such as coupled resonator optical waveguides (CROW), also known as coupled-cavity waveguides (CCW). Another example is effective refractive index guiding, as provided by ridge or rib waveguides, or large width photonic crystal channel waveguides with more than two rows of defects. Depending on the waveguide mechanism, mode and phase matching structures at the extremities of the waveguides can be defined to improve the coupling between adjacent system blocks.

Figure 6:
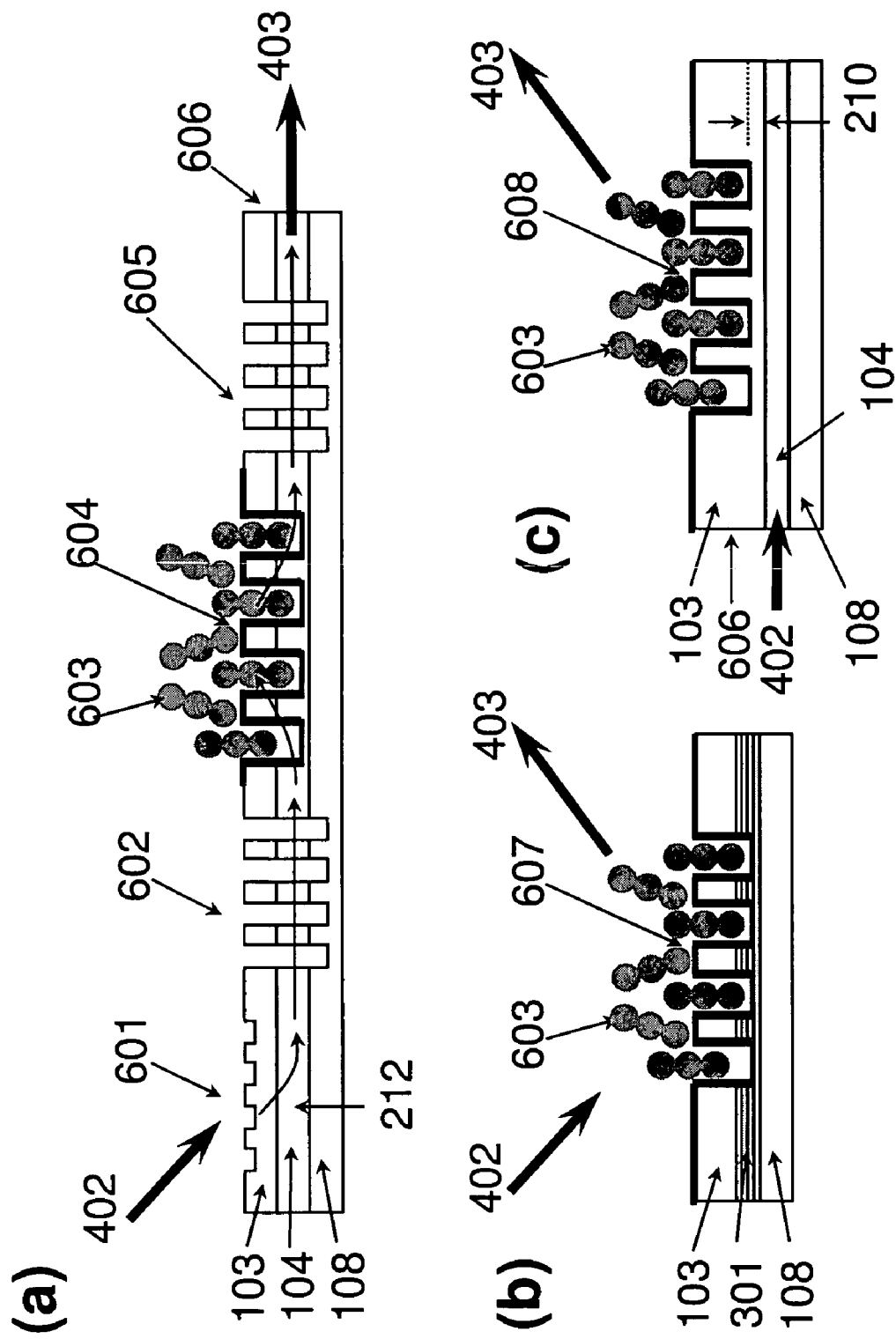
FIG. 6 illustrates three exemplary embodiments in which one or more functional system units are either integrated on chip (a) or combined to form a new structure that incorporates more than one functionality (b) and (c) with the same structure.
Figure 7:
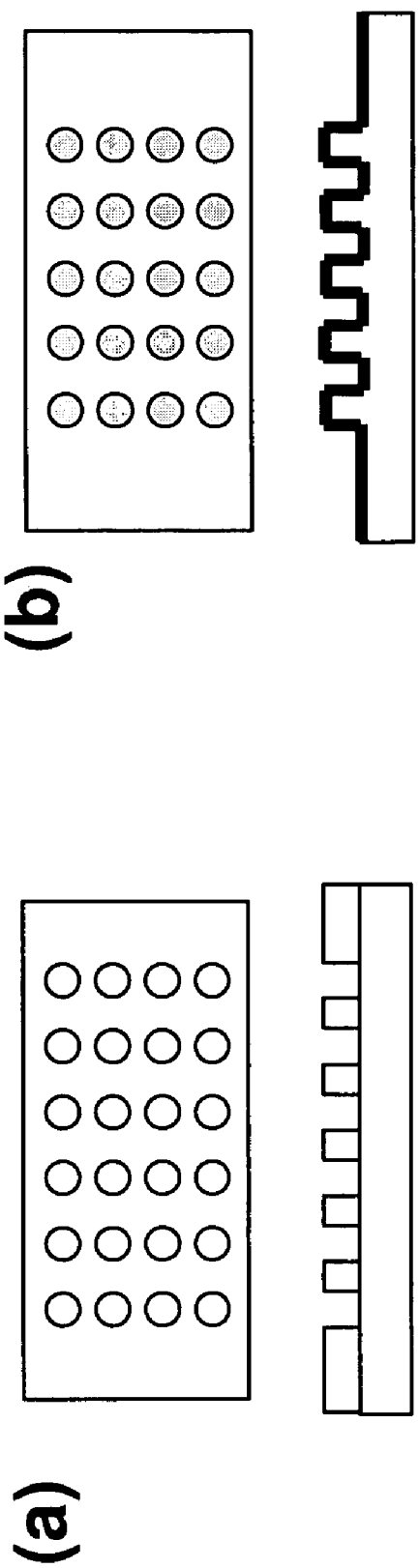
FIG. 7 shows two examples of prior art systems.

FIG. 6 illustrates three exemplary embodiments of an integrated platform. FIG. 6(*a*) shows a platform that incorporates (from left to right) a structure 601 for receiving optical radiation, a preprocessing unit 602 for example to select a favourable polarization state, the platform 604 for generating the Raman signal, a postprocessing unit 605 that for examples filters out the pump light, and a cleaved facet 606 to extract the Raman signal. The dielectric multilayer structure located underneath the SERS active region forms a planar waveguide structure 212 to transport the light from one functional block to the other. Light 402 is incident at structure 601, which has been designed to receive optical radiation and the incident light's in-plane wavevector component is coupled to the planar waveguide 212 where it is guided to a PC-based preprocessing section 602. After passing through said pre-processing unit 602, the light has a defined polarization state. The polarized light couples to the SPPs, which in turn excite vibrational modes of the analyte molecules 603 located in close proximity to the active SERS region 604. The Raman signal emerging from the SERS active region is coupled back into the waveguide 212 and passes through a postprocessing unit 605 that for example filters out the wavelength of the incident optical radiation 402 and is guided to a cleaved facet 606 from where the light 403 can be extracted.

FIG. 6(*b*) illustrates a monolithically integrated device in which the structure for receiving and extracting the optical radiation and the active structure for generating the Raman signal are integrated into one photonic crystal section 607. The incident light 402 of a predefined polarization state is coupled to the SERS active region of the platform from out-of-plane. By exploiting the photonic band structure properties and coupling the light into the desired Bloch modes, while at the same time interacting with the SP modes, several operations can be performed simultaneously. The Raman enhanced electromagnetic signal 403 that emerges from the platform is collected from the same side from which the platform has received radiation, i.e. the measurement is performed in the reflection regime. The polarization state of the incident light can be defined by passing the light through an external polarization filter. In this embodiment, the platform preferably comprises a multilayer mirror structure 301 located underneath the photonic crystal SERS active surface with a band stop overlapping the desired Raman signal to reflect the Raman signal and direct it into the reflection regime. This configuration represents the preferred embodiment for the SERS active platform.

FIG. 6*c* depicts a third embodiment in which a cleaved facet 606 serves as the structure for receiving optical radiation. The incident electromagnetic radiation 402 is guided from the entry facet 606 through a planar waveguide structure 212 and coupled to the photonic band structure, which in turn couples into the SP modes of the SERS active region. The spacing between the photonic band structure and the waveguide determines the coupling strength: the smaller the distance, the stronger the coupling. The SERS active region and the structure for extracting optical radiation are integrated into one structural unit 608. The Raman signal 403 emerging from the SERS active region is collected out-of-plane for postprocessing and detection.

System

Figure 10:
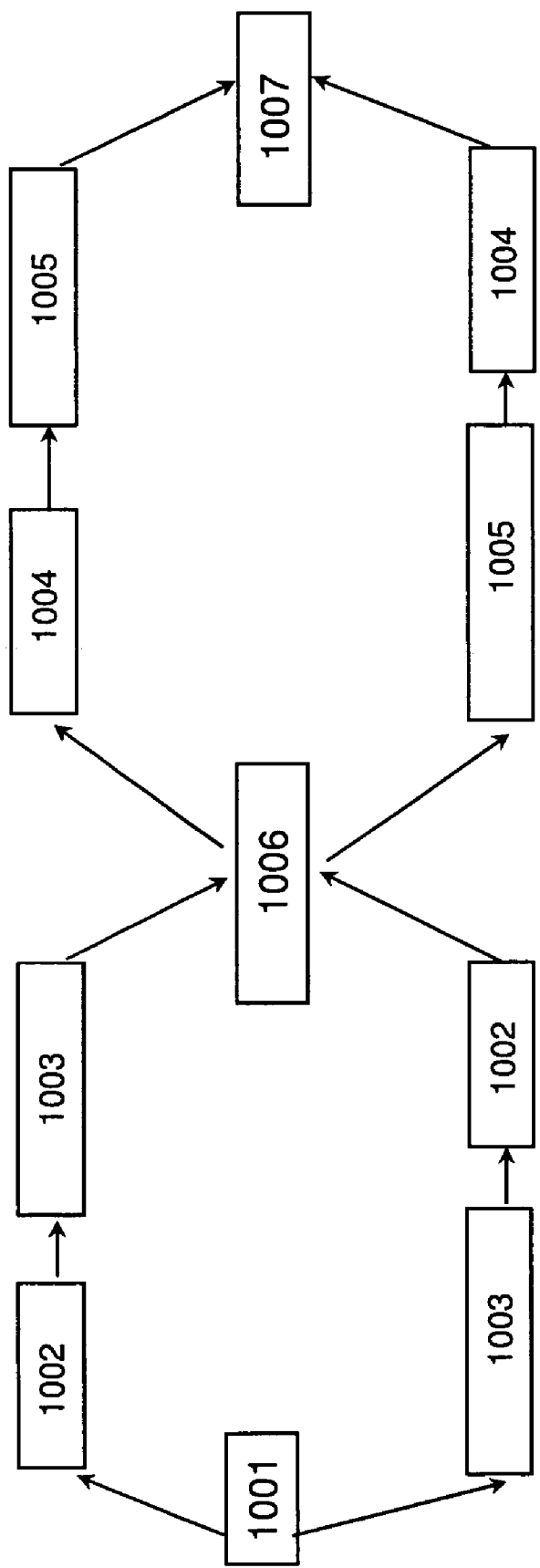
FIG. 10 schematically illustrates the system for obtaining a Raman signal from an analyte under investigation.

In a second aspect, a system for the detection and analysis of analytes is provided, as schematically illustrated in FIG. 10. The system provides a Raman enhanced signal such that less incident radiation can be used while still obtaining an acceptable signal-to-noise ratio (SNR) compared to standard Raman measurements.

The system comprises a light source 1001 that emits electromagnetic radiation, a functional unit 1002 that pre-processes the optical signal, a structure 1003 for receiving optical radiation, a structure 1006 for generating the Raman signal, a functional unit 1004 that postprocesses the Raman enhanced signal, a structure 1005 for extracting optical radiation, and a sensor 1007 to detect the Raman enhanced electromagnetic radiation. The units for preprocessing 1002 and receiving 1003 the optical radiation and the units for postprocessing 1004 and extracting 1005 the optical radiation can be interchanged as schematically illustrated in FIG. 10 through the alternative branches, i.e. the functional pre-/postprocessing units can be integrated into the device or can be external to the device.

The preprocessing function depicted in FIG. 10 can include a polarization control and/or filtering of the incident EM radiation, which can be achieved either externally through individual polarizers and optical filters or in-plane. If coupling light in-plane, the preprocessing can be monolithically integrated with the SERS active platform onto one chip as previously discussed in the context of the platform. For example, a PC section can be defined in-plane such that it serves as a wavelength or polarization filter.

The postprocessing unit can filter the pump light to improve the SNR, can filter the desired polarization state for detection, or can be used to spatially resolve the different energies of the emitted photons, hence serve as a monolithically integrated spectral analyzer. If the Raman signal is detected in-plane, it can for example be guided to a separate PC section that penetrates the waveguide core to act as a superprism, polarization filter, or spectral filter. Alternatively, the PC lattice that constitutes the SERS active region can be defined such that the propagation direction of the SPPs is very sensitive to their respective energies.

One can therefore identify two types of component integration that can independently result in a miniaturization of the system setup and reduced number of required components that constitute the system. Firstly, functional blocks may be integrated with the SERS active region onto the same chip. Secondly, adjacent functional blocks that are defined on the same biochip may be combined into one structural element.

Examples of the first integration type have been illustrated in FIG. 6(a). Besides those already mentioned, it is furthermore possible to integrate the active components of the system, namely the light source for emitting optical radiation and the sensor for detecting the SERS signal onto the biochip by defining active regions located adjacent to the passive waveguide regions, therefore eliminating the need for an external light source and/or external photodetector.

Examples of the second integration type are illustrated in FIGS. 6(b) and (c). The adjacent functional blocks of receiving and/or extracting the optical radiation and generating the Raman signal are integrated into one structural element 607 and 608, respectively.

It is therefore possible to monolithically integrate many of the functional blocks depicted in FIG. 10 into a monolithically integrated device, thus reducing the number of individual components forming the system, therefore saving space and component cost.

Method

In a third aspect, a method for the detection and analysis of an analyte is provided, which uses the platform and system described above. The method is schematically illustrated in FIG. 9. An analyte molecule is brought (851) in proximity to the PC SERS active region. A light source is turned on (852) and its electromagnetic radiation is passed through a preprocessing unit. The settings of the preprocessing unit is adjusted (853) to couple light of predefined incident parameters such as wavelength, polarization state, and/or incident angles to the SERS active region either from the region above the surface or from a planar waveguide structure located underneath the surface.

The light excites various plasmonic states that can couple to one another and that can transfer energy to different vibrational modes of the adsorbate molecule. The Raman signal is collected, passed through a postprocessing unit, and detected (854) either in-plane or out-of-plane, depending on the selected system configuration, using a spectrometer or other means as outlined above.

Figure 16A:
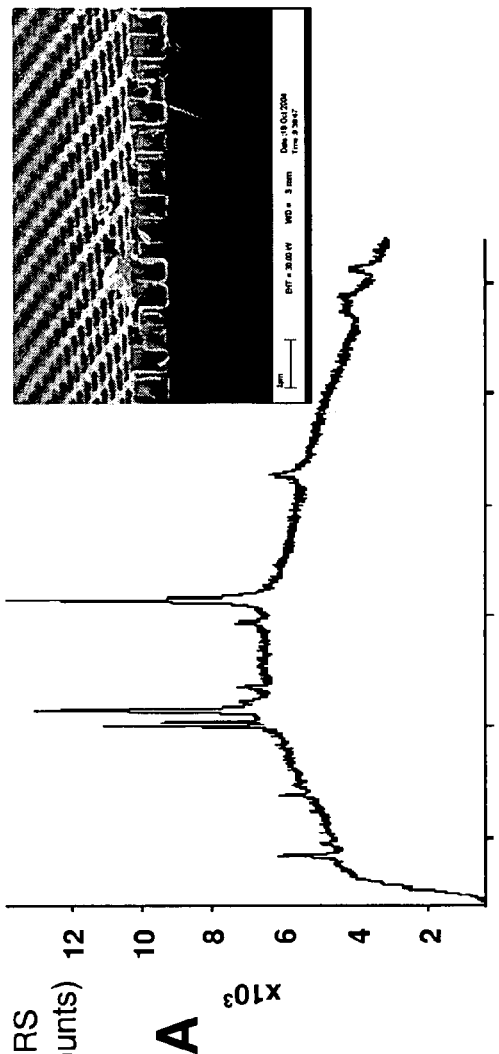
FIGS. 16A, B and C illustrate the repeatability of several experimental Raman signals from a self assembled monolayer of benzenethiol when placed on the surface of three types of PC-SERS substrate (SEMs shown in the inserts).

FIGS. 16A, B and C show the experimental Raman signals detected using the claimed PC-SERS substrate in terms of counts versus wavenumber. A self-assembled monolayer (SAM) of Benzenethiol is located on the surface of the PC-SERS substrate and is detected using a Renishaw Raman spectrometer. SEM micrographs of the PC-SERS structures are shown in the inserts to FIGS. 16A, B and C. The metal coating on all the structures is nominally 300 nm.

In the structure shown in FIG. 16A, the SERS active region comprises a metal coated square lattice air rod photonic crystal region. The lattice pitch of the air rods is approximately 600 nm, which is approximately an order of magnitude larger scale than prior art structures associated with SERS enhancement due to roughness corrugations (~50 nm). As illustrated, the Raman signal from Benezenethiol SAM highlights the feasibility of detection of SERS from the PC-SERS substrate. These structures are typically lithographically defined using expensive direct write electron beam lithography, or alternatively nanoimprinting, due to their small-scale dimension.

Figure 16B:
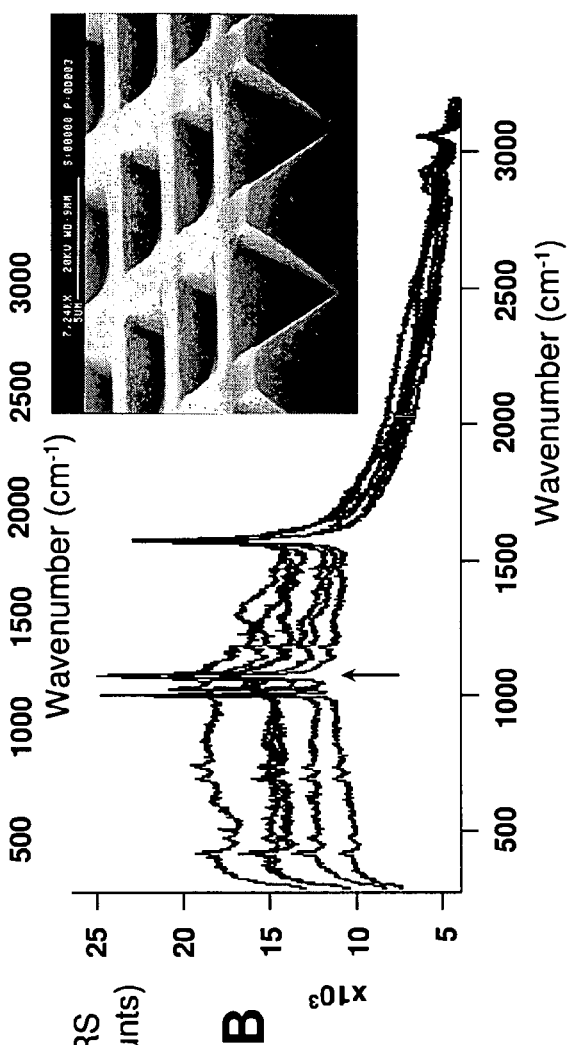
FIG. 16B depicts the experimental SERS results from an inverted pyramidal PC-SERS substrate.
Figure 16C:
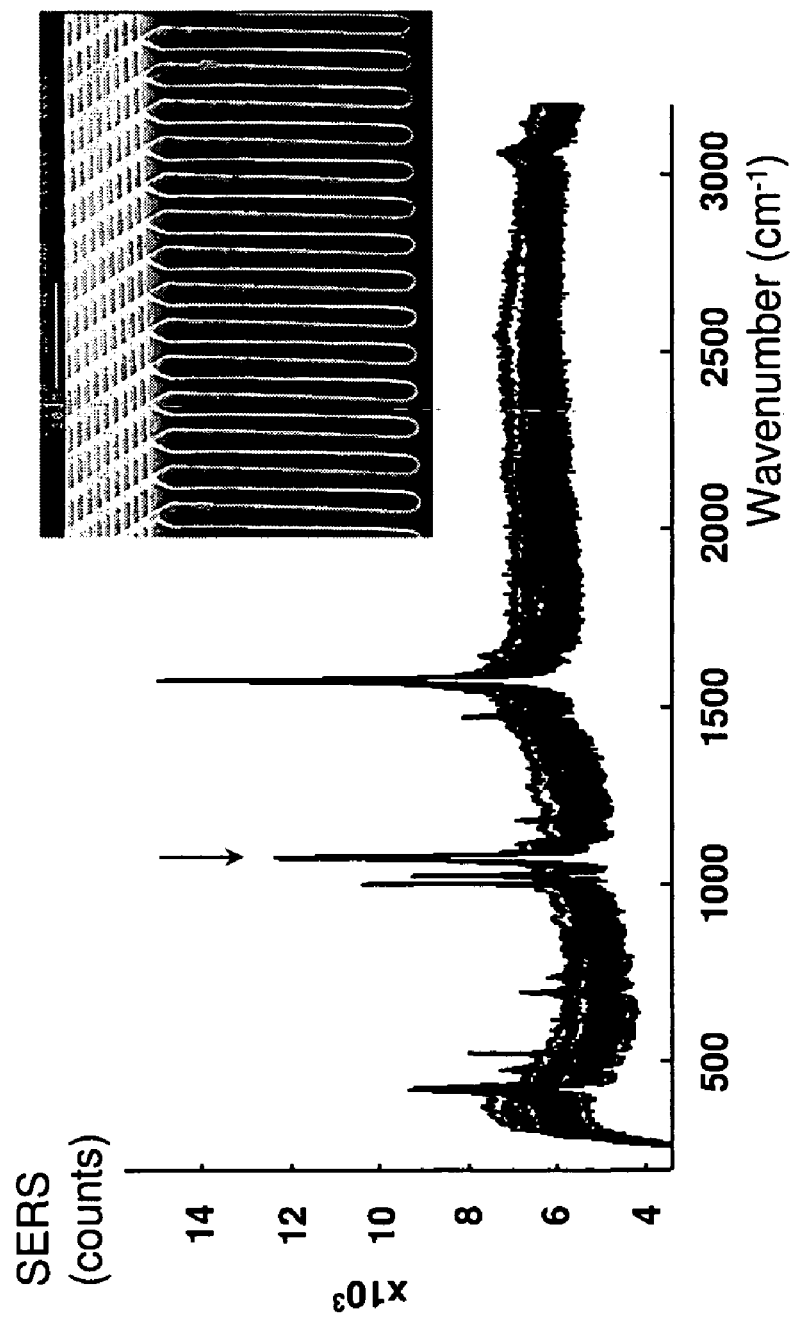
FIG. 16C shows the repeatability of the Raman signal from a PC-SERS substrate with deep etched (high aspect ratio) holes.

For more cost effective fabrication, the structure shown in FIG. 16B is composed of a metal-coated modulated photonic crystal surface comprising inverted pyramids arranged on a 2 micron pitch, while the structure shown in FIG. 16C is composed of a metal-coated corrugated surface comprising inverted pyramids with deeply-etched cylindrical holes located at the apex of the inverted pyramid. These structures can be defined using low cost photolithography. The deep (high aspect ratio) cylindrical holes are typically deeper than 40 μm and in this example are of 6 μm pitch with 0.3 μm of Gold metal coating. To highlight the excellent reproducibility, several Raman signals for the benzenethiol SAM are collected at 25 different locations around a 25 μm by 25 μm area of the PC-SERS substrate and superimposed on the same plot. The relative standard deviation of the peak heights at 1071 $cm^{-1}$ against the background level for the different experiments is calculated as 7.0% for the high aspect ratio structures and 9.9% for the inverted pyramid structures. It is also noticed that the background in the Raman signals (characterised by the broad background signal detected across a large wavenumber range) can be greatly reduced depending on the PC-SERS structure used. In particular, the high aspect ratio structures shown in FIG. 16C dramatically reduce the effect. This is attributed to the Raman signal being efficiently coupled out of plane in a directional fashion contrary to the nondirectional scattered background signal.

In order to characterise the potential contribution to the SERS signal arising from surface roughness corrugations in the PC-SERS active region, a high resolution Field Emission Gun SEM (FEG-SEM) of the metal coated inverted pyramidal SERS structure was obtained, as shown in FIG. 17A. It can be seen that the roughness on the sidewalls are of the order of 70 nm with air cavities of the order of 20 nm surrounding microcolumns with depth 50 nm to 100 nm.

For control comparison, the SERS effect of a Benzenethiol SAM on a flat unpatterned gold layer with identical rough surface corrugation was investigated. The resulting measured SERS signal is shown in FIG. 17B (an SEM of the surface is shown in the inset). The dotted line indicates the Raman spectra acquired using the same acquisition time and settings as used in the experiments that yielded the results of FIGS. 16A, B and C, while the solid line indicates an acquisition time 6 times longer. The clear lack of any Raman signature implies that the Benzenthiol is not detected and therefore the flat roughened gold surface under investigation is not a SERS active substrate.

However, when the dispersion properties of the metal coated inverted pyramidal SERS structure of FIG. 17A is examined in detail, many strong features attributable to the long scale patterned plasmonic bandstructure are apparent.

FIG. 17C shows the results of a reflectivity experiment in which collimated laser light of varying wavelength is incident on the structure at different incident angles. Plasmon energy (and therefore angular frequency) is plotted against angle of incidence θ. The resulting contour map represents the 2D plasmonic dispersion diagram of the inverted pyramid PC-SERS substrate. The faint lines 1706 indicate the coupling of incident light into the distinct diffraction modes associated with the large-scale periodic modulation of the structure. However, the discrete complicated pattern of islands 1703 originate from the surface and localisation plasmons and are attributed to the metal coated inverted pyramid structures. When light is coupled into these localised plasmon regions, SERS can be achieved. During the selection of the PC-SERS parameters, the location and abundance of these islands can be tailored to optimise the SERS effects giving rise to highly reproducible SERS signals.

Experiments have been performed on structures with PC pitches varying from 0.4 µm to 6 µm and the structures have shown excellent reproducibility with a variation of less than 15% from sample to sample.

In FIG. 18F the effect of matching the localised plasmon resonance to the pump laser wavelength on the SERS signal is evident. In this experiment, a monolayer coverage of 4-aminothiophenol is attached to graded inverted pyramidal substrates similar to those described with reference to FIG. 18A. From the plot of FIG. 18F, it can be clearly seen that the SERS signal (in counts) for the 1080 $cm^{-1}$ line is greatly enhanced as the localised plasmon is brought into resonance with the excited pump laser light by varying the inverted pit depth in micrometers.

In another aspect, FIG. 19 demonstrates the plan view of a fabrication tolerant and wavelength insensitive metallodielectric photonic crystal structure comprising but not restricted to an array of sub-regions of inverted pyramids. The sub-region defined by 1901 and 1902 in the horizontal direction and the vertical direction consists of multiple inverted polyhedra of different sizes arranged on the same pitch 1903. Each inverted polyhedra within a sub-region provides a different localised plasmon resonance and hence allows optimal field localisation for a diverse range of operating input laser wavelengths. Additionally, the range of localised plasmon resonances allows the output Raman light of different wavelengths to couple back into the plasmon resonances and propagate to the output coupling regions. To improve reproducibility of the SERS signal, the incident laser spot size 1904 is allowed to overlap at least one sub-region.

Fabrication Method

In the fourth aspect, a method for fabricating the SERS active platform is provided. The fabrication process is schematically illustrated in FIGS. 8A(a)-(k) and comprises an epitaxial growth step, a pattern definition stage, a highly anisotropic etch process, and a metal evaporation stage.

Figure 8A:
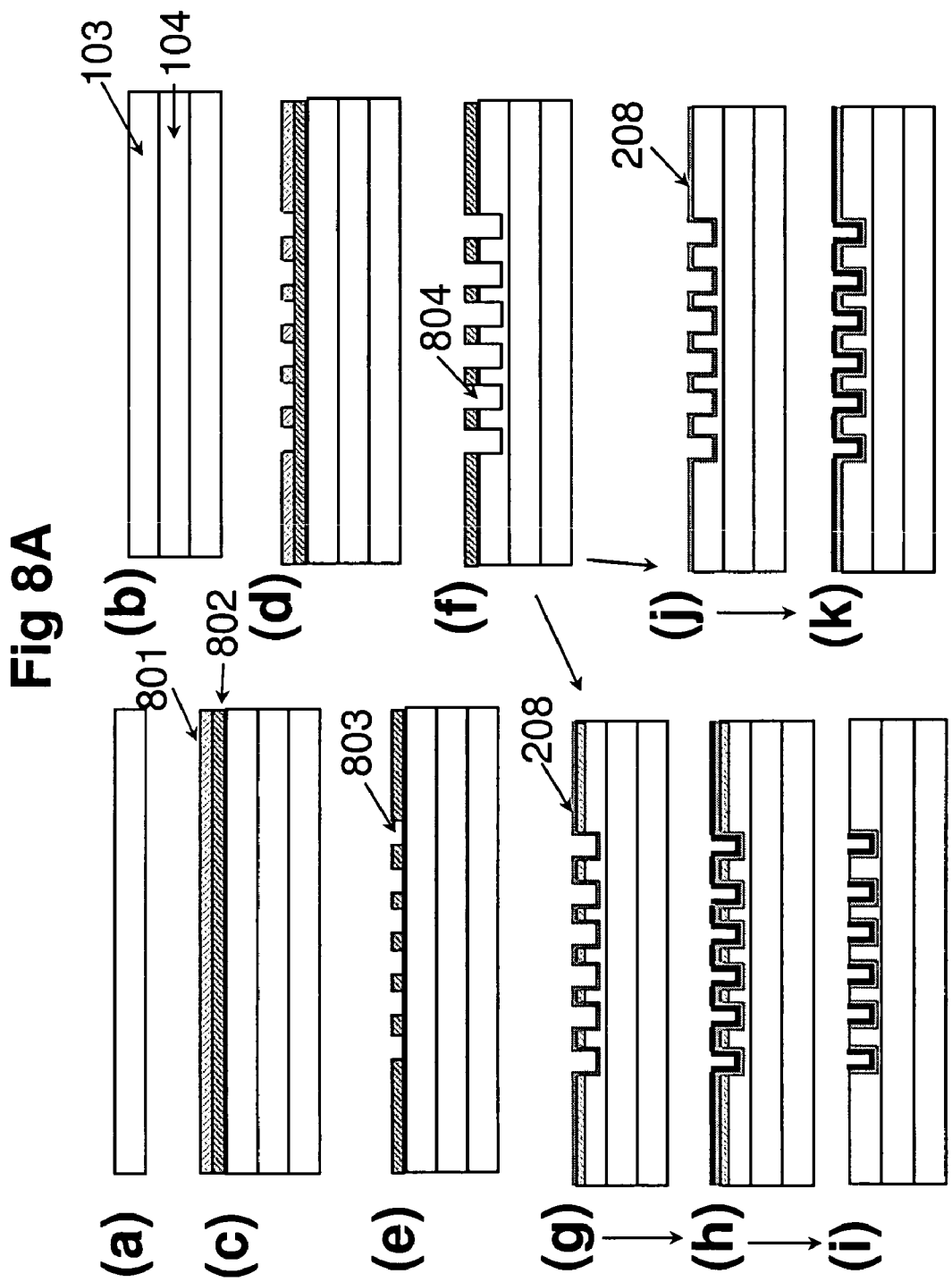
FIG. 8A illustrates a fabrication process to produce the SERS active platforms.

In a first step depicted in FIG. 8A(b), the multilayered dielectric structure 104, 104 is epitaxially grown on top of the substrate 108 (FIG. 8A(a)) to form for example a multilayer mirror structure or a waveguide structure. The epitaxial growth technology can be selected from, but is not restricted to, the following group of technologies: molecular beam epitaxy (MBE), Metal Organic Vapor Phase Epitaxy (MOVPE), gas source molecular beam epitaxy (GSMBE/Chemical Beam Epitaxy (CBE)/Metal Organic Molecular Beam Epitaxy (MOMBE), Liquid Phase Epitaxy (LPE), atomic layer epitaxy (ALE), hydride (or halide) vapour-phase epitaxy (HVPE), vapour growth, solid phase epitaxy.

In a second step depicted in FIG. 8A(c), an etch mask layer 802 is preferably deposited onto the organically cleaned surface of the cladding 103 followed by a resist layer 801. The etch mask layer 802 can consist of a dielectric or metallic material and its thickness is chosen such that it will act as a shadow mask in the etch process later until the desired etch depth is approached. The mask material can be deposited using for example a vacuum sputtering or electron beam evaporation process.

Subsequently, the pattern can be defined in the resist (FIG. 8A(d)) using one of the following methods: photolithography, electron beam lithography, interference lithography, or imprint lithography followed by the development of the resist. The pattern is then transferred to the etch mask (FIG. 8A(e)) using a highly selective etch process that selectively removes the etch mask 802 while not etching into the upper-strata material 103.

Using a second, highly anisotropic etch process, the holes or wells 804 are transferred into the substrate using the perforated layer 803 as a shadow etch mask as illustrated in FIG. 8A(f). The following exemplary etch processes can be used for this purpose: electron cyclotron resonance assisted reactive ion etching (ECR-RIE), chemically assisted ion beam etching (CAIBE), inductive coupled plasma reactive ion etching (ICP-RIE), ion beam milling or anodic etching.

Depending on whether it is desired to have a metallic coating on top of the substrate surface or not, the remainder of the etch mask is either removed or kept, respectively. If removing of the etch mask is desired as schematically illustrated in FIG. 8A(j), it can be accomplished employing either a dry or wet etch process.

Figure 12:
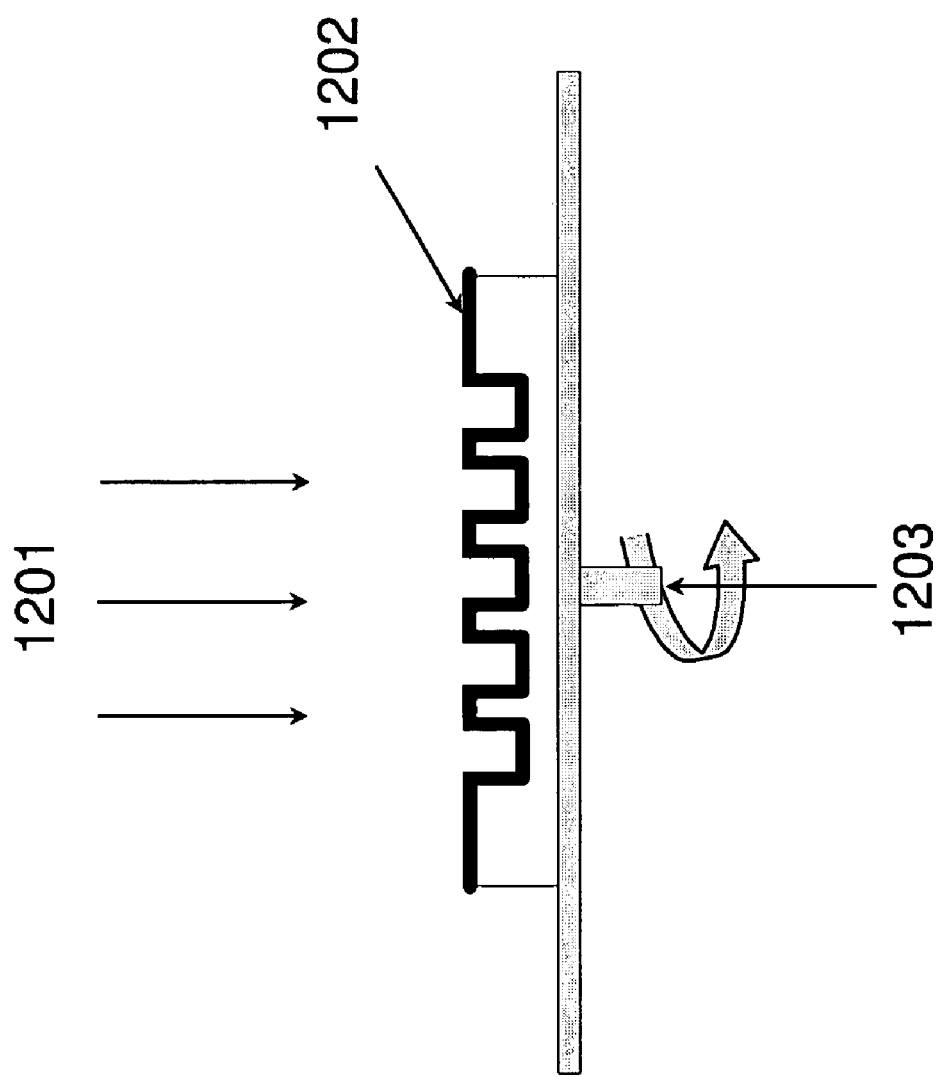
FIG. 12 illustrates the deposition process of the metallodielectric layer.

An adhesion layer 208, for example a monolayer of Chromium or Mercapto-propyl-trimethoxysilane is deposited onto the metal surface as depicted in FIGS. 8A(g) and 8(j) to improve the bonding of the noble metal to the substrate. The noble metal is then deposited or plated (electroplating and electro-less plating) on top of the adhesive layer on top of the sample 103 and the inside the holes 105 and 106 (FIG. 8A(h) and FIG. 8A(k)). In order to ensure that the structures possess a metallodielectric layer on the bottom and the sides of the air rods, the particle flow 1201 is tilted against the normal of the substrate surface by an appropriate angle as illustrated in FIG. 12. The construction 1203 on which the substrate 1202 is mounted is then rotated continuously while the material is deposited onto the sample. If the etch mask was not removed previously, it is removed now to form isolated metal-coated 105, 106 air holes (FIG. 8A(i)).

Depending on the method of metal deposition or plating, the roughness corrugations in the metallodielectric layer can be controlled. These are typically in the small-scale roughness range, of the order of 10 nm-100 nm. The roughness can be controlled by the fabrication deposition process conditions, which can affect the roughness scale and dimensions. Examples of relevant parameters include the rate of deposition, temperature of substrate, r.f. power level and chamber vacuum pressure. The depth of the rough corrugations can also depend on the thickness of the deposited metallodielectric layer.

Figure 13:
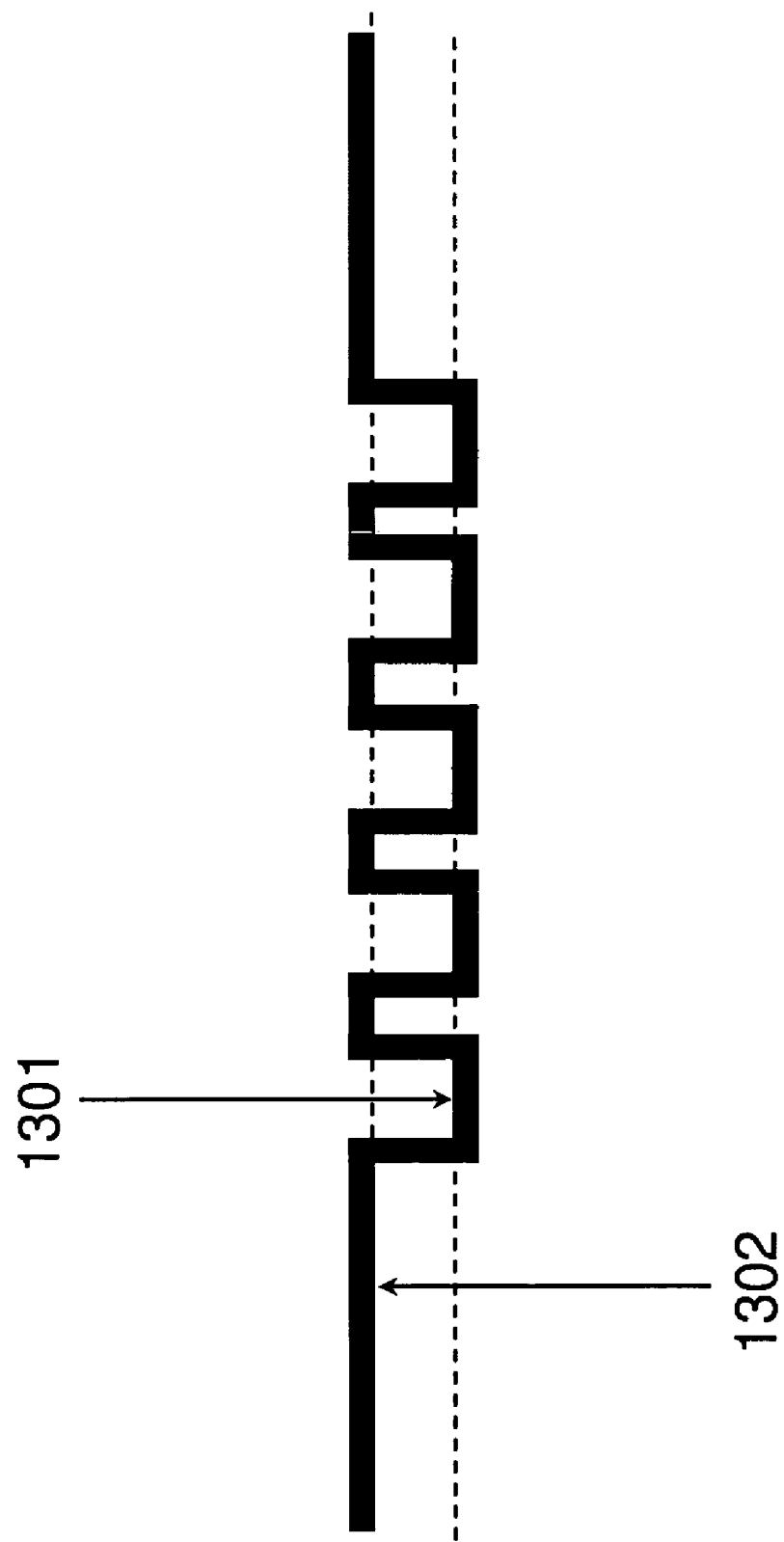
FIG. 13 presents a schematic illustration of the fabricated SERS structure.

The fabricated structure will possess a metallodielectric surface profile modulation as schematically illustrated in FIG. 13, in which the top surface 1301 of the metallodielectric-coated holes are lower that the top surface 1302 of the underlying dielectric structure.

Figure 8B:
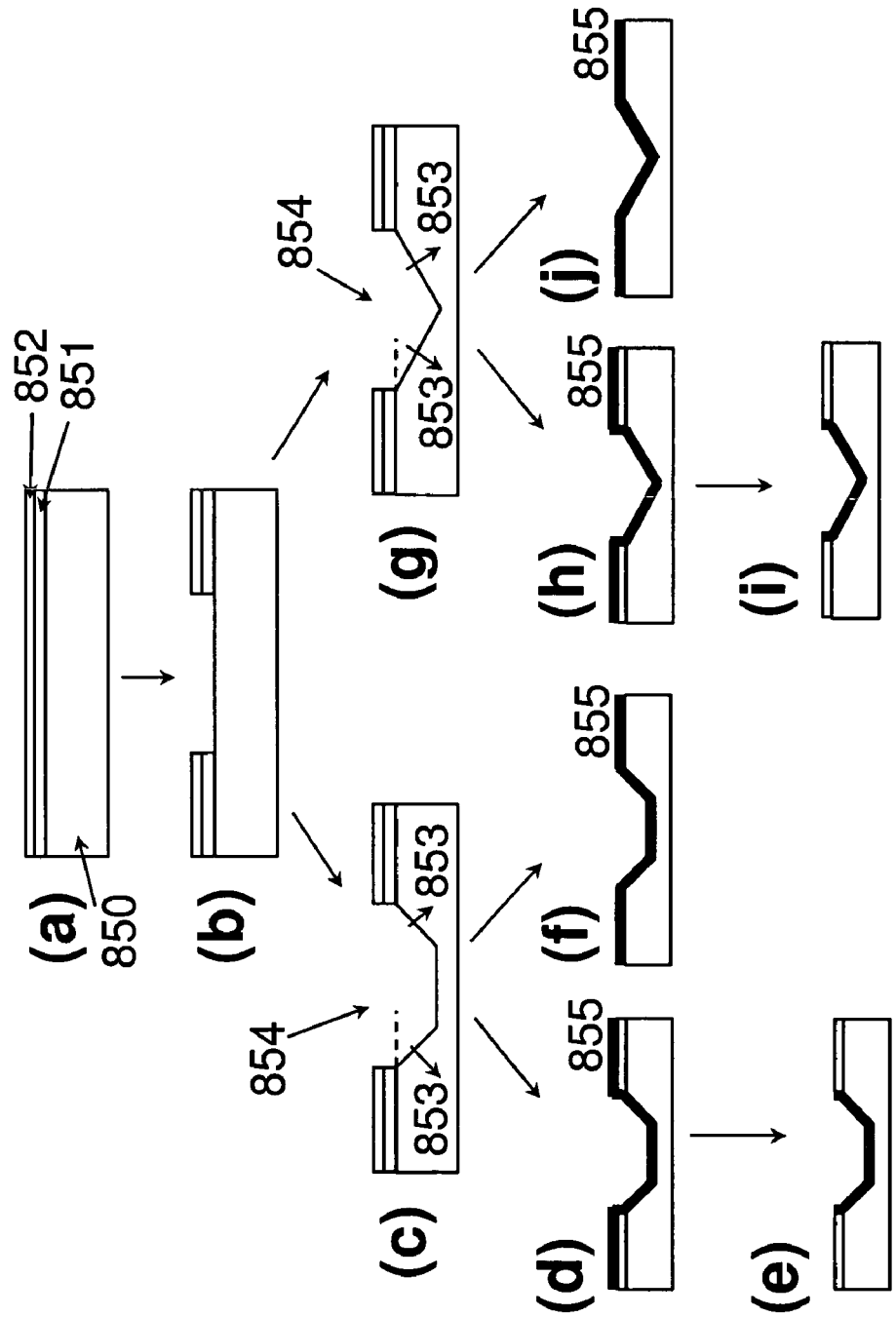
FIGS. 8B(a)-(j) illustrate a fabrication process when anisotropic etching of single crystal Silicon wafers is employed to produce the SERS active platforms. While FIG. 8B(k) depicts the anisotropic wet etching properties of inverted pyramids when etched through a mask.

In another method of fabrication anisotropic wet etching is employed to define the hole/well following the resist pattern definition. Anisotropic wet etching is a well known technique and is commonly used in the MEMs area. Preferential etching along specific planes of single crystal Silicon is employed to define predetermined inverted polyhedral structures onto the surface of the substrate. The shapes are determined by selecting the crystal orientation of the Silicon wafer, resist pattern and the etch duration. The etch process will stop once all inverted polyhedra faces are along the {111} crystal planes of the substrate. In the simplest form, a {100} single crystal wafer surface 850 is selected as shown in FIG. 8B(a). An etch mask layer 851 is preferably deposited onto the organically cleaned surface of the single crystal Silicon. The etch mask layer 851 can consist of a dielectric material selectively resistant to the anisotropic wet etch. These are typically Silicon Nitride or Silicon Dioxide. Subsequently, the pattern can be defined into the resist 852 and then transferred into the mask (FIG. 8B(b)) using one of the previously discussed techniques.

Using the anisotropic wet etch process, the wells 854 are formed as shown in FIG. 8B(c) and FIG. 8B(g). Some examples of wet etch process chemicals used for anisotropic wet etching are EDP (ethylenediamine pyrocatechal), CsOhH, KOH, NaOH or N2H4-H2O (Hydrazine). It is also noted that the rate of etching can also be controlled by temperature and concentration. In the case of the {100} surface oriented wafer, when the etch is allowed to come to a natural stop, an inverted pyramidal structure is formed. The angle made between the top surface (as shown by the dashed line in FIG. 8B(c) and FIG. 8B(g)) of the substrate and the angled facet is about 54°. The location of the inverted pyramids is determined by the location of the etched sub-regions in the mask. However, it is noted that if the anisotropic wet etch is allowed to naturally stop, the shape of elements in the array on the mask become irrelevant and structures such as FIG. 8B(g) are formed. The shape of the inverted polyhedra formed is ultimately determined by the orientation of the Silicon crystal planes and, in the case of {100}, inverted pyramids are formed. The size of the inverted pyramids will depend on the size of the mask sub-regions 857 and will expand out until the perimeter of the sub-region is completely enclosed by the pyramid base 856 as shown in FIG. 8B(k). If the anisotropic wet etching is allowed to end prematurely, then more complicated truncated pyramidal structures form. This is shown in FIG. 8B(c) for a {100} crystal substrate orientation.

In another preferred embodiment, following the anisotropic wet etching, an additional etch step is also additionally performed. This provides the combined inverted pyramidal-hole structure as shown FIG. 8B(l). The cross-section of the hole 858 takes on the shape of the etch mask sub-regions (as in 857). The etching can be performed using highly anisotropic reactive ion etching, ion beam milling or anodic etching. Structures with more than a 10:1 hole depth to lattice pitch can be achieved.

As previously mentioned, depending on whether a metallic coating on the top substrate surface is required or not, the remainder of the etch mask is either removed or kept, as shown in FIGS. 8B(d) and (f), and FIGS. 8B(h) and (j), respectively. If removing of the etch mask is desired, as schematically illustrated in FIGS. 8B(e) and (i), it can be accomplished employing either a dry or wet etch process.

Following the definition of the inverted polyhedra and high aspect ratio holes, the steps of the deposition of the metal layer remains identical to those previously described, in relation to FIG. 8A.

What is claimed is:

1. A planar optical platform for generating a Raman signal from a foreign object; comprising:
    an input region for receiving optical radiation;
    a plasmonic band structure region optically coupled to the input region, the plasmonic band structure region comprising a layer of a first material patterned with an array of sub-regions of a second material, the first material having a first refractive index and the second material having a second refractive index, a side-wall of each sub-region being coated with a metallic or metallodielectric layer, wherein the array of sub-regions give rise to a plasmonic band structure, and wherein, in use, each sub-region confines at least one plasmon resonance excited by optical radiation coupled into the plasmonic band structure region which gives rise to a Raman signal from a foreign object placed proximate the plasmonic band structure region; and
    an output region for extracting optical radiation, the output region optically coupled to the plasmonic band structure region.

2. A platform according to claim 1, wherein an end-wall of each sub-region is coated with a metallodielectric layer.

3. A platform according to claim 1, wherein unpatterned regions of the layer of the first material are coated with a metallodielectric layer.

4. A platform according to claim 1, wherein the sub-regions are located at the vertices of a predefined tiling arrangement selected from a group consisting of: a periodic lattice of square, rectangular or triangular geometry, a quasiperiodic tiling, an amorphous tiling, a graded lattice, a doubly-graded lattice, a superposition of two tiling arrangements and a tiling arrangement possessing single or multiple defect sub-region sites.

5. A platform according to claim 1, wherein at least one sub-region comprises a circular or elliptical cylinder having a diameter from 5 nm to about 10,000 nm and a cylinder depth from 1 nm to 10,000 nm.

6. A platform according to claim 1, wherein at least one sub-region comprises an inverted polyhedron or an inverted truncated polyhedron having a base length ranging from 50 nm to about 20,000 nm.

7. A platform according to claim 6, wherein at least one sub-region comprises an inverted polyhedron or an inverted truncated polyhedron contiguous with a circular-, elliptical- or polygonal-faced cylinder, the maximum diameter of the cylinder being smaller than the polyhedron base length.

8. A platform according to claim 6, wherein the polyhedron comprises a pyramid.

9. A platform according to claim 1, wherein a transverse extent of each of the sub-regions varies across the array.

10. A platform according to claim 1, wherein the second material comprises air.

11. A platform according claim 1, wherein the first material is selected from a group consisting of silicon, silicon dioxide, silicon nitride, silicon oxynitride, tantalum pentoxide, polymer, and a semiconductor material.

12. A platform according to claim 1, wherein the metallic or metallodielectric layer has a thickness of from 1 nm to 500 nm.

13. A platform according to claim 1, wherein the metallic layer or the metallodielectric layer comprises one or more metallic layers comprising a metal selected from a group consisting of gold, platinum, silver, copper, palladium, cobalt, iron and nickel.

14. A platform according to claim 1, wherein a surface of the metallic or metallodielectric layer is rough due to the coating fabrication method.

15. A platform according to claim 1, further comprising a multi-layered planar metallodielectric or dielectric structure on which the patterned layer is disposed.

16. A platform according to claim 15, wherein the multi-layered structure comprises one of a planar distributed-Bragg reflector, a planar optical waveguide and a one-dimensional photonic crystal stack.

17. A platform according to claim 15, wherein the multi-layered structure comprises a material selected from a group consisting of silicon, silicon dioxide, silicon nitride, silicon oxynitride, tantalum pentoxide, polymer and a semiconductor material.

18. A platform according to claim 15, wherein the sub-regions extend though part of the multi-layered structure.

19. A platform according to claim 15, wherein the multi-layered structure comprises an air void directly below the sub-regions.

20. A platform according to claim 16, wherein the input region comprises a portion of the planar optical waveguide.

21. A platform according to claim 1, wherein the input region comprises a portion of the plasmonic band structure region which, in use, diffractively couples optical radiation into the plasmonic band structure region.

22. An optical device comprising a platform according to claim 1 further comprising a processing structure optically-coupled to the plasmonic band structure region for preprocessing optical radiation incident on the platform and coupling the preprocessed radiation to the plasmonic band structure region or a processing structure optically-coupled to the plasmonic band structure region for postprocessing optical radiation coupled from the plasmonic band structure region to the postprocessing structure.

23. An optical device according to claim 22, wherein the processing structure performs one or more functionalities selected from a group consisting of polarization filtering, spectral filtering, optical time delay, super-diffraction, beam steering and beam collimation.

24. An optical device according to claim 22, wherein the processing structure is selected from a group consisting of a taper coupler, an evanescent coupler, a velocity taper coupler, a grating structure, a one-dimensional photonic crystal, a periodic two-dimensional photonic crystal and a two-dimensional photonic quasicrystal.

25. An optical device according to claim 22, wherein the processing structure is formed integrally with the plasmonic band structure region.

26. An optical system for performing Raman spectroscopy on a foreign object comprising;
an optical source;
an optical platform for generating a Raman signal from a foreign object, comprising:
an input region for receiving optical radiation,
a plasmonic band structure region optically coupled to the input region, the plasmonic band structure region comprising a layer of a first material patterned with an array of sub-regions of a second material, the first material having a first refractive index and the second material having a second refractive index, a side-wall of each sub-region being coated with a metallic or metallodielectric layer, wherein the array of sub-regions give rise to a plasmonic band structure, and wherein, in use, each sub-region confines a plasmon resonance excited by optical radiation coupled into the plasmonic band structure region which gives rise to a Raman signal from a foreign object placed proximate the plasmonic band structure region, and
an output region for extracting optical radiation, the output region optically coupled to the plasmonic band structure region,
the optical platform optically coupled to the optical source; and
an optical detector optically coupled to the optical platform for detecting a Raman signal generated when the foreign object is placed proximate the plasmonic band structure region into which radiation from the optical source is coupled.

27. A method for obtaining a Raman or surface enhanced Raman spectrum from a sample foreign object, the method comprising the steps of:
locating the sample foreign object proximate the plasmonic band structure region of an optical platform, wherein the platform comprises
an input region for receiving optical radiation,
a plasmonic band structure region optically coupled to the input region, the plasmonic band structure region comprising a layer of a first material patterned with an array of sub-regions of a second material, the first material having a first refractive index and the second material having a second refractive index, a side-wall of each sub-region being coated with a metallic or metallodielectric layer, wherein the array of sub-regions give rise to a plasmonic band structure, and wherein, in use, each sub-region confines a plasmon resonance excited by optical radiation coupled into the plasmonic band structure region which gives rise to a Raman signal from a foreign object placed proximate the plasmonic band structure region, and
an output region for extracting optical radiation, the output region optically coupled to the plasmonic band structure region, the optical platform optically coupled to the optical source;
activating an optical source generating optical radiation optimised for excitation of surface plasmons, an optimised parameter for said radiation selected from a group which includes wavelength, azimuthal and polar angles, and polarization state;
coupling the optical radiation into the plasmonic band structure region; and,
detecting a spectrum of a Raman signal emerging from the optical platform.

28. A method according to claim 27, wherein the step of locating the foreign object comprises flowing the foreign object in a fluid in the vicinity of the plasmonic band structure region.

29. A method according to claim 28, wherein the foreign object comprises a molecule of an analyte selected from a bio-chemical group consisting of chemical warfare agents, pesticides, urea, lactic acid, pollutants, ascorbate, glucose, or a biomolecule selected from a group which includes proteins, lipids, nucleic acids such as bacterial and viral DNA, RNA, PNA, and biological cells such as cancer cells.

30. A method according to claim 29, wherein the foreign object is located within 50 nm of one of the sub-regions in the plasmonic band structure region.

31. A method for fabricating an optical platform comprising an input region for receiving optical radiation, a plasmonic band structure region optically coupled to the input region, the plasmonic band structure region comprising a layer of a first material patterned with an array of sub-regions of a second material, the first material having a first refractive index and the second material having a second refractive index, a side-wall of each sub-region being coated with a metallic or metallodielectric layer, wherein the array of sub-regions give rise to a plasmonic band structure, and wherein, in use, each sub-region confines at least one plasmon resonance excited by optical radiation coupled into the plasmonic band structure region which gives rise to a Raman signal from a foreign object placed proximate the plasmonic band structure region, and an output region for extracting optical radiation, the output region optically coupled to the plasmonic band structure region, the method comprising the steps of:

epitaxially growing the layer of the first material and any underlying multi-layered structure;

defining a pattern on the layer of the first material;

etching a portion of the epitaxial structure with an anisotropic etch; and depositing a metallic or metallodielectric layer.

32. A method according to claim 31, wherein the pattern definition step is selected from a group of techniques consisting of photolithography, deep UV lithography, electron beam lithography, interference lithography, imprint or stamping process.

33. A method according to claim 31, wherein the etching step comprises highly anisotropic plasma etching performed using a technique selected from a group consisting of reactive ion etching (RIE), electron cyclotron resonance assisted reactive ion etching (ECR-RIE), chemically assisted ion beam etching (CAIBE), and inductive coupled plasma reactive ion etching (ICP-RIE).

34. A method according to claim 31, wherein the etch step comprises highly anisotropic anodic etching.

35. A method according to claim 31, wherein the etching step is highly anisotropic and comprises ion beam milling.

36. A method according to claim 31, wherein the anisotropic etch is a wet etch process using a chemical selected from a group consisting of: EDP (ethylenediamine pyrocatechal), CsOhH, NaOH, N2H4-H2O (Hydrazine) and KOH.

37. A method according to claim 36, wherein the first material is single crystal silicon and the anisotropic etch is terminated when the crystal planes of the Silicon are completely exposed along all the faces of an inverted polyhedron.

38. A method according to claim 31, further comprising an additional wet etch step, wherein the additional step also uses a chemical selected from a group consisting of: EDP (ethylenediamine pyrocatechal), CsOhH, NaOH, N2H4-H2O (Hydrazine) and KOH.

39. A method according to claim 31, wherein the metal deposition step is performed using a technique selected from a group consisting of physical vapour deposition (PVD), evaporation deposition, chemical vapour deposition (CVD), and atomic layer deposition (ALD).

* * * * *